(12) United States Patent
Hales et al.

(10) Patent No.: US 7,538,096 B2
(45) Date of Patent: May 26, 2009

(54) TREATMENT AND PREVENTION OF ABNORMAL CELLULAR PROLIFERATION

(75) Inventors: Charles A. Hales, Lincoln, MA (US); Hari G. Garg, Belmont, MA (US); Lunyin Yu, Allston, MA (US); Robert J Linhardt, Albany, NY (US)

(73) Assignees: The General Hospital Corporation, Boston, MA (US); The University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/082,213

(22) Filed: Mar. 16, 2005

(65) Prior Publication Data

US 2005/0288251 A1 Dec. 29, 2005

Related U.S. Application Data

(60) Provisional application No. 60/553,800, filed on Mar. 16, 2004.

(51) Int. Cl.
*A61K 31/727* (2006.01)
(52) U.S. Cl. .............................. 514/56; 514/54; 536/21
(58) Field of Classification Search .................. 514/56, 514/54; 536/21; 623/23.7
See application file for complete search history.

(56) References Cited

U.S. PATENT DOCUMENTS 5,820,917 A * 10/1998 Tuch .......................... 427/2.1
6,130,210 A 10/2000 Caretto et al.
6,203,536 B1 3/2001 Berg et al.

FOREIGN PATENT DOCUMENTS

WO WO 88/01280 2/1988

OTHER PUBLICATIONS

Barzu et al. (European Journal of pharmacology (1992), 219 (2), 225-33).*
Yu et al. (FASEB Abstracts, Mar. 17, 2003).*
Gura (Science, 1997, 278(5340):1041-1042).*
Jain (Sci. Am., 1994, 271 :58-65).*
Curti (Crit. Rev. in Oncology/Hematology, 1993, 14:29-39).*
Centeno Cortés et al. (Lung Cancer 1997; 18 (1): 101-105).*
Database STN Abstract: Accession No. 1992:584605; European Journal of Pharmacology; 219(2):225-33 (1992) (see abstract).
Database STN Abstract: Accession No. 1996:49022; Oncology Reports; 3(1):219-22 (1996) (see abstract).
Tereza Barzu, et al.; European Journal of Pharmacology; 219 (1992) 225-233.
Tereza Barzu, et al.; J. Med. Chem. 1993, 36, 3546-3555.
Dierdre R. Coombe, et al.; Int. J. Cancer: 39, 82-88 (1987).
Christopher R. Parish, et al. Int. J. Cancer: 40, 511-518 (1987).
Lanyin Yu, et al.; FASEB Abstracts, Mar. 17, 2003.

* cited by examiner

*Primary Examiner*—Shaojia Anna Jiang
*Assistant Examiner*—Michael C Henry
(74) *Attorney, Agent, or Firm*—Nixon Peabody LLP

(57) ABSTRACT

This invention provides a method for inhibiting or preventing the abnormal growth of cells, including transformed cells, by administering an effective amount of O-acylated heparin derivative. Abnormal growth of cells refers to cell growth independent of normal regulatory mechanism (e.g. loss of contact inhibition). This includes the abnormal growth of: (1) tumor cells (tumors); (2) benign and malignant cells of other proliferative disease in which aberrant cellular proliferation occurs; (3) aberrant smooth muscle cell proliferation, such as might occur following treatment for coronary atherosclerosis such as angioplasty or the insertion of a stent into an occluded vessel.

4 Claims, 24 Drawing Sheets

HEXANOYL DERIVATIVE OF LMW HEPARIN R=$CH_3(CH_2)_4$-
BUTANOYL DERIVATIVE OF LMW HEPARIN R=$CH_3(CH_2)_2$-

TREATMENT AND PREVENTION OF ABNORMAL CELLULAR PROLIFERATION

CROSS REFERENCE TO RELATED APPLICATIONS

The present application claims benefit under 35 U.S.C. § 119(e) of U.S. Provisional Application Ser. No. 60/553,800 filed Mar. 16, 2004, the content of which is herein incorporated by reference in its entirety.

GOVERNMENT SUPPORT

This invention was made in part with U.S. Government support under grant number 5 RO1 HL39150-15 awarded by the National Institutes of Health. The U.S. Government has certain rights in this application.

FIELD OF INVENTION

The present invention is directed to a method of treating or preventing abnormal cellular proliferation.

BACKGROUND OF THE-INVENTION

Atherosclerosis, a common form of arteriosclerosis, results from the deposition of fatty substances, primarily cholesterol, and subsequent fibrosis in the inner layer (intima) of an artery, resulting in plaque deposition on the inner surface of the arterial wall and degenerative changes within it. The ubiquitous arterial fatty plaque is the earliest lesion of atherosclerosis and is a grossly flat, lipid-rich atheroma consisting of macrophages (white blood cells) and smooth muscle fibers. The fibrous plaque of the various forms of advanced atherosclerosis has increased intimal smooth muscle cells surrounded by a connective tissue matrix and variable amounts of intracellular and extracellular lipid. At the luminal surface of the artery, a dense fibrous cap of smooth muscle or connective tissue usually covers this plaque or lesion. Beneath the fibrous cap, the lesions are highly cellular consisting of macrophages, other leukocytes and smooth muscle cells. As the lesions increase in size, they reduce the diameter of the arteries and impede blood circulation resulting in coronary heart disease, myocardial infarction (MI) and other serious complications.

Many therapies have been considered for the treatment of atherosclerosis, including surgery and medical treatment. One potential therapy is percutaneous transluminal angioplasty (balloon angioplasty). More than 400,000 such procedures are performed each year in the United States. In balloon angioplasty, a catheter equipped with an inflatable balloon is threaded intravascularly to the site of the atherosclerotic narrowing of the vessel. Inflation of the balloon compresses the plaque enlarging the vessel.

While such angioplasty has gained wider acceptance, it suffers from two major problems, i.e., abrupt closure and restenosis. Abrupt closure refers to the acute occlusion of a vessel immediately after or within the initial hours following a dilation procedure. Abrupt closure occurs in approximately one in twenty cases and frequently results in myocardial infarction and death if blood flow is not restored in a timely manner.

As many as 50% of the patients who are treated by balloon angioplasty require a repeat procedure within six months to correct a re-narrowing of the artery. Restenosis refers to such re-narrowing of an artery after an initially successful angioplasty. Restenosis of the blood vessel is thought to be due to injury to the endothelial cells of the blood vessel during angioplasty, or during inflation of the balloon catheter. During healing of the blood vessel after surgery, smooth muscle cells proliferate faster than endothelial cells resulting in a narrowing of the lumen of the blood vessel and starting the atherosclerotic process anew. In recent years, smooth muscle cell proliferation has been recognized as a major clinical problem limiting the long-term efficacy of coronary angioplasty.

In an effort to prevent restenosis of the treated blood vessel, the search for agents that can reduce or prevent excessive proliferation of smooth muscle cells have been the object of much research. (The occurrence and effects of smooth muscle cell proliferation after these types of surgery have been reviewed, for example, in Ip, et al., (June 1990) J. Am. College of Cardiology 15:1667-1687, and Faxon, et al. (1987) Am. J. of Cardiology 60: 5B-9B.). Such compounds have found little if any practical success. There therefore exists a need to identify and successfully administer compounds that inhibit smooth muscle cell proliferation.

An alternative to angioplasty is the placement of endovascular stents in the occluded blood vessel. Placement of a stent at such a site, should mechanically block abrupt closure and delay restenosis (Harrison's Principles of Internal Medicine, 14$^{th}$ Edition, 1998). Of the various procedures used to overcome restenosis, stents have proven to be the most effective. Stents are metal scaffolds that are positioned in the diseased vessel segment to create a normal vessel lumen. Placement of the stent in the affected arterial segment prevents recoil and subsequent closing of the artery. By maintaining a larger lumen than that created using balloon angioplasty alone, stents reduce restenosis by as much as 30%. Despite their success, stents have not eliminated restenosis entirely. (Suryapranata et al. 1998. Randomized comparison of coronary stenting with balloon angioplasty in selected patients with acute myocardial infarction. Circulation 97:2502-2502).

Unfortunately, the use of such stents are limited by direct (subacute thrombosis) or indirect (bleeding, peripheral vascular complications) complications. After stent implantation the patients are threatened with stent thrombosis until the struts of the stent are covered by endothelium. Thus, an aggressive therapy using anticoagulation and/or antiplatelet agents is necessary during this period of time. While these therapies are able to decrease the rate of stent thrombosis, they are the main source of indirect complications.

In addition to coronary artery occlusion, narrowing of the arteries can occur in other vessels. Examples include the aortoiliac, infrainguinal, distal profunda femoris, distal popliteal, tibial, subclavian and mesenteric arteries. The prevalence of peripheral artery atherosclerosis disease (PAD) depends on the particular anatomic site affected as well as the criteria used for diagnosis of the occlusion. Rates of PAD appear to vary with age, with an increasing incidence of PAD in older individuals. Data from the National Hospital Discharge Survey estimate that every year, 55,000 men and 44,000 women had a first-listed diagnosis of chronic PAD and 60,000 men and 50,000 women had a first-listed diagnosis of acute PAD. Ninety-one percent of the acute PAD cases involved the lower extremity. The prevalence of comorbid coronary artery disease (CAD) in patients with PAD can exceed 50%. In addition, there is an increased prevalence of cerebrovascular disease among patients with PAD.

PAD can be treated using percutaneous transluminal balloon angioplasty (PTA). The use of stents in conjunction with PTA decreases the incidence of restenosis. However, the postoperative results obtained with medical devices such as stents do not match the results obtained using standard operative revascularization procedures, i.e., those using a venous or prosthetic bypass material. (Principles of Surgery, Schwartz et al. eds., Chapter 20, Arterial Disease, 7th Edition, McGraw-Hill Health Professions Division, New York 1999).

Preferably, PAD is treated using bypass procedures where the blocked section of the artery is bypassed using a graft. (Principles of Surgery, Schwartz et al. eds., Chapter 20, Arterial Disease, 7th Edition, McGraw-Hill Health Professions Division, New York 1999). The graft can consist of an autologous venous segment such as the saphenous vein or a synthetic graft such as one made of polyester, polytetrafluoroethylene (PTFE), or expanded polytetrafluoroethylene (ePTFE). Restenosis and thrombosis, however, remain significant problems even with the use of bypass grafts. For example, the patency of infrainguinal bypass procedures at 3 years using an ePTFE bypass graft is 54% for a femoral-popliteal bypass and only 12% for a femoral-tibial bypass.

Consequently, there is a significant need to improve the performance of both stents and synthetic bypass grafts in order to further reduce the morbidity and mortality of CAD and PAD.

With stents, the approach has been to coat the stents with various anti-thrombotic or anti-restenotic agents in order to reduce thrombosis and restenosis. For example, impregnating stents with radioactive material appears to inhibit restenosis by inhibiting migration and proliferation of myofibroblasts. (U.S. Pat. Nos. 5,059,166, 5,199,939 and 5,302,168). Irradiation of the treated vessel can pose safety problems for the physician and the patient. In addition, irradiation does not permit uniform treatment of the affected vessel.

Numerous attempts to develop stents with a local drug-distribution function have been made, most of which are variances of the so called stent graft, a metal stent covered with polymer envelope, containing a medicament. It would be of benefit to coat a stent with a compound capable of diminishing or eliminating restenosis.

Unlike the unwanted smooth muscle cell proliferation seen in restenosis, cellular proliferation is a normal ongoing process in all living organisms and is one that involves numerous factors and signals that are delicately balanced to maintain regular cellular cycles.

When normal cellular proliferation is disturbed or somehow disrupted, the results can be inconsequential or they can be the manifestation of an array of biological disorders. Disruption of proliferation could be due to a myriad of factors such as the absence or overabundance of various signaling chemicals or presence of altered environments. Some disorders characterized by abnormal cellular proliferation include cancer, abnormal development of embryos, improper formation of the corpus luteum, difficulty in wound healing as well as malfunctioning of inflammatory and immune responses.

Cancer is characterized by abnormal cellular proliferation. Cancer cells exhibit a number of properties that make them dangerous to the host, often including an ability to invade other tissues and to induce capillary ingrowth, which assures that the proliferating cancer cells have an adequate supply of blood. One of the defining features of cancer cells is that they respond abnormally to control mechanisms that regulate the division of normal cells and continue to divide in a relatively uncontrolled fashion until they kill the host.

It is clear that aberrant cellular proliferation plays a major role in the formation and progression of a cancer. If this abnormal or undesirable proliferative activity could be repressed, inhibited, or eliminated, then the tumor, although present, would not grow. In the disease state, prevention of abnormal or undesirable cellular proliferation could slow or abate the progression of cancer. Additionally, compounds that could induce apoptosis of abnormally proliferating cells would be especially beneficial for complete removal or elimination of malignant cells, helping to reduce relapses. Therapies directed at control of the cellular proliferative processes could lead to the abrogation or mitigation of such malignancies.

Pulmonary hypertension is caused largely by an increase in pulmonary vascular resistance and is classified clinically as either primary or secondary. Secondary pulmonary hypertension, the more common form, is generally a result of (1) chronic obstructive or interstitial lung disease; (2) recurrent pulmonary emboli; (3) liver disease; or (4) antecedent heart disease. Primary pulmonary hypertension is diagnosed only after all known causes of increased pulmonary pressure are excluded.

At the moment there is no successful cure for pulmonary hypertension. Administration of vasodilatating drugs has not proved to be useful in patients suffering from pulmonary hypertension. The prognosis is poor, with a median survival time of about 3 years.

Pulmonary fibrosis can occur in response to known stresses such as asbestos or silica but most is idiopathic. There is a spectrum of idiopathic fibrosis but most kinds are fatal in 3-5 years. At present, there is no effective therapy for most cases.

What is needed therefore is a composition and method which can inhibit abnormal or undesirable cellular proliferation, especially the growth of smooth muscle cells after angioplasty, stent placement, pulmonary hypertension, pulmonary fibrosis or the proliferation of malignant cells. The composition should be able to overcome the activity of endogenous growth factors in premetastatic tumors and inhibit smooth muscle cell proliferation during restenosis. Finally, the composition and method for inhibiting cellular proliferation should preferably be non-toxic and produce few side effects.

Heparin is a glycosaminoglycan that was first described by McLean in 1916 and has been used clinically as an anticoagulant for more than 50 years [McLean, Circulation 19, 75-78 (1959)]. Members of the glycosaminoglycan family include hyaluronan, heparan sulfate, dermatan sulfate, and chondroitin sulfate. Beyond its well-recognized anticoagulant activity, heparin has other activities. The antimetastatic activity of heparin has been known for some time (see, for example, Drago, J. R. et al., Anticancer Res., 4(3), 171-2, 1984).

Unfortunately, native and currently described modified heparins are extremely anticoagulant. Their anticoagulant properties are such that doses effective in the treatment of malignancies and anti-proliferative disorders are not attainable. It has therefore been suggested that altering the chemical structure of heparin might decrease the anticoagulant properties of heparin while maintaining its other important biological activities, such as its antimetastatic activity (Barzu et al., J. Med. Chem, 1993, 36, pg. 3546-3555).

Low molecular weight heparins have shown promise in reducing anticoagulation while maintaining their antimetastatic activity. For example, when compared to unmodified heparin, 2-O-desulfated and 3-O-desulfated heparins had reduced anticoagulant activities, but preserved their angiostatic, anti-tumor and anti-metastatic properties (Masayuki et al., U.S. Pat. No. 5,795,875 (1997); Lapierre et al., Glycobiology 6, 355-366 (1996)]. Nevertheless, the use of currently available heparins and heparin derivitives for the treatment of abnormal cellular proliferative disorders is not practical due to their marked anticoagulant and antithrombotic activities.

O-acylated heparins have been described. These molecules have very low anticoagulative effects in vitro, yet retain activity against HIV-1 and 2 induced cytopathicity (Barzu et al., J. Med. Chem, 1993, 36, pg. 3546-3555).

A chemically modified heparin that can be used to treat and/or prevent abnormal cellular proliferative disorders is needed. Such a compound should have minimal anticoagulant properties while maintaining antiproliferative properties. The anticoagulative properties of the compound must not limit its use in the clinical setting.

SUMMARY

This invention provides a method for inhibiting or preventing the abnormal growth of cells, including transformed cells, by administering an effective amount of O-acylated heparin derivative. Abnormal growth of cells refers to cell growth independent of normal regulatory mechanism (e.g. loss of contact inhibition). This includes the abnormal growth of: (1) tumor cells (tumors); (2) benign and malignant cells of other proliferative disease in which aberrant cellular proliferation occurs; (3) aberrant smooth muscle cell proliferation, such as might occur following treatment for coronary atherosclerosis such as angioplasty or the insertion of a stent into an occluded vessel. The O-acylated heparin derivative is preferably an O-hexanoylated heparin derivative or an O-butanoylated heparin derivative. In a preferred embodiment, the o-acylated heparin is weakly anticoagulant as compared to non-chemically modified heparins.

One embodiment of the present invention provides a method for inhibiting or preventing tumor growth by administering an effective amount of an o-acylated heparin, to a subject, e.g. a mammal (and more particularly a human) in need of such treatment. In particular, this invention provides a method for inhibiting the growth of malignant cells by the administration of an effective amount of an O-acylated heparin. In a preferred embodiment, the methods are directed toward the treatment or prevention of lung and colon cancer. Preferably, the O-acylated heparin derivative is an O-hexanoylated or an O-butanoylated heparin derivative In another embodiment, the invention provides a method of preventing abnormal smooth muscle cell proliferation. The method comprises presenting an O-acylated heparin near or into a site of abnormal smooth muscle cell proliferation. In a preferred embodiment, the methods are directed toward the prevention of smooth muscle cell proliferation as occurs in restenosis. The methods are used to prevent restenosis that occurs following angioplasty or vascular stent placement. Alternatively, the methods of the current invention are used to prevent restenosis following coronary artery stent placement, peripheral artery stent placement, or cerebral artery stent placement.

In yet another embodiment, the invention provides a medical device coated with the heparin composition, e.g., a stent for implantation in a blood vessel. The stent of the invention comprises a coating containing an O-acylated heparin and preferably, an O-hexanoylated or O-butanoylated heparin derivative. In one embodiment, the stent is coated with an O-acylated heparin and one or more compounds selected from the group consisting of a polymer, fiber polymer, polyurethane, silicone rubber elastomer, drug, hydrogel, or other acceptable compound or carrier known to those of skill in the art. Other medical devices such as catheters may also be coated with the O-acylated heparin.

Finally, the invention provides a method of treating pulmonary hypertension and pulmonary fibrosis. The methods of the present invention provide treating a subject with a therapeutic amount of an o-acylated heparin, preferably a O-hexanoylated or O-butanoylated heparin derivative. In one embodiment, the invention provides for the treatment of primary pulmonary hypertension. In another embodiment, the invention provides for the treatment of secondary pulmonary hypertension. In a final embodiment, the invention provides for the treatment of pulmonary fibrosis.

DESCRIPTION OF FIGURES

FIG. 23A, a stent; FIG. 23B, an end view of the stent of FIG. 23A

DETAILED DESCRIPTION

The present invention is directed generally to compositions and their use in the therapy and prevention of abnormal cellular proliferative disorders, such as cancer, (i.e. lung and colon cancer), restenosis (following angioplasy, vascular stent placement, coronary artery stent placement, periphaeral artery stent placement, or cerebral artery stent placement), pulmonary hypertension (primary or secondary), and pulmonary fibrosis. The administration of therapeutic levels of the O-acylated heparin derivatives result in a decrease, cessation, or prevention of the abnormal cellular proliferation.

O-Acylated Heparin

As described further below, compositions useful in the present invention include, but are not restricted to, O-acylated heparins, particularly O-hexanoylated heparin derivatives and O-butanoylated heparin derivatives.

Figure 3:
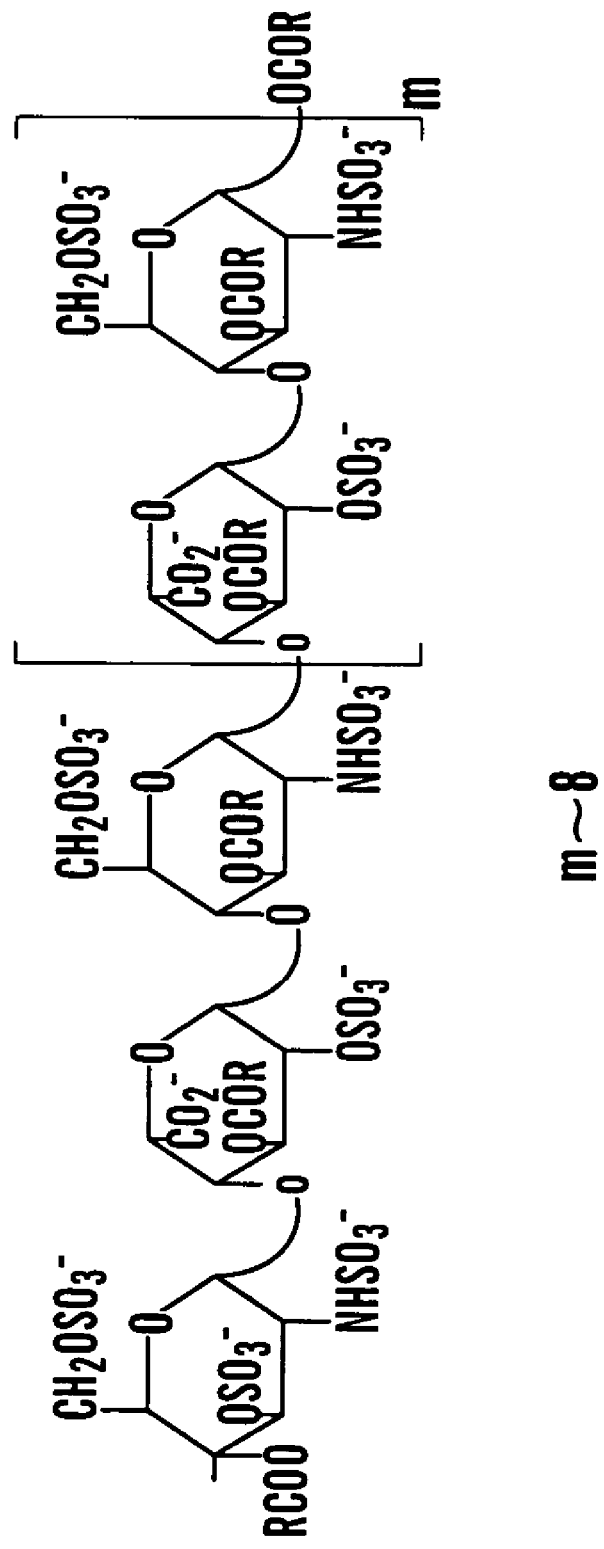
FIG. 3 shows the structures of O-hexanoylated heparin and O-butanoylated heparin.

O-acylated heparins are prepared using any of a variety of well known synthetic and/or recombinant techniques, an example of which is further described below. Furthermore, O-acylated heparins, useful in the present invention, have been described in Barzu et al., J. Med. Chem, 1993, 36, 3546-3555 and U.S. Pat. No. 4,990,502 (Lormeau et al.). The structure of the O-acylated heparin derivatives used in the present invention are shown in FIG. 3. Preferably, the major disaccharide units (m) vary from about 4 to about 14. Most preferably the major disaccharide units (m) vary from about 7 to about 9. In the O-hexanoylated derivative, $R=CH_3(CH_2)_4$- in the O-butanoylated derivative, $R=CH_3(CH_2)_2$-.

Low-molecular weight heparins (LMWHs) are fragments of conventional heparin. LMWHs were developed to provide more selective inhibition of enzyme function and reduce adverse effects. Heparin fragmentation produces products which maintain activity against factor $X_a$ and release antithrombotic factors, but have significantly less activity against factor $II_a$. As a result, treatment with LMWHs provides antithrombotic effects with less anticoagulant effect, lessening the risk of hemorrhage. However, in the generic sense, LMWHs have not proven beneficial in the treatment of cancer due to their high anticoagulant activity.

Administration of Compounds

The heparins of the present invention can be administered via any medically acceptable means which is suitable for the compound to be administered, including oral, rectal, topical, parenteral (including inhaled, subcutaneous, intramuscular and intravenous) administration, or by coated stent, coated graft, or coated catheter.

Effective doses for heparin-like substances are well known to those of skill in the art. Generally, for heparin-like substances, an effective dose is that which maintains the anti-$X_a$ level between 0.5 and 1.0 units/ml. This range has been shown to optimize antithrombotic activity while avoiding adverse effects.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. If discrete multiple doses are indicated, treatment might typically be 4-6,000 units of a compound given 4 times per day or if given continuously, as is more often the case, then a loading dose of 80 units/kg followed by 18 units/kg/hr (Rascke R A, Reilly B M, Guidry J R, et al. The weigh based heparin dosing nomogram compared with a "standard care" nomogram: A randomized control trial. Ann Int Med 119:874-81, 1993).

Formulations

The compounds described above are preferably administered in a formulation including an O-acylated heparin and/or an O-acylated heparin-together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the O-acylated heparin can be formulated into a liposome or microparticle which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGFβ, basic fibroblast growth factor (bFGF), epithelial growth factor (EGF), transforming growth factors alpha and beta (TGFα and TGFβ), nerve growth factor (NGF), platelet-derived growth factor (PDGF), and vascular endothelial growth factor/vascular permeability factor (VEGF/VPF), antivirals, antibacterials, antiinflammatories, immunosuppressants, analgesics, vascularizing agents, cell adhesion molecules (CAM's), and anticoagulants other than heparin or heparin-like substances.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Finally, compositions of the compound are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, more preferably between 2 and 5 microns.

Stents, Grafts and Implants

The present invention further provides an intravascular implant coating. The coating includes a therapeutically effective amount of an O-acylated heparin. The coating can be used in any type of implant. These include balloon catheters, stents, stent graphs, drug delivery catheters, atherectomy devices, filters, scaffolding devices, anastomothic clips, anastomotic bridges and suture materials.

The coating can also include a polymer matrix, with the polymer being a resorbable polymer selected from the group consisting of poly-α hydroxyl acids, polyglycols, polytyrosine carbonates, starch, gelatins, cellulose, and blends and copolymers thereof. Examples of suitable poly-α hydroxyl acids include polylactides, polyglycol acids, and blends and co-polymers thereof.

According to the present invention, a coating for an intravascular implant is provided. The coating can be applied either alone, or within a polymeric matrix, which can be biostable or bioabsorbable, to the surface of an intravascular device. The coating can be applied directed to the implant or on top of a polymeric substrate, i.e. a primer. If desired, a top coat can be applied to the therapeutic coating.

It should be noted that the present invention relates to a combinatorial therapy for delivery of more than one agent through a coating on any intravascular implant. As used herein, implant means any type of medical or surgical implement, whether temporary or permanent. Delivery can be either during or after an interventional procedure. Non-limiting examples of intravascular implants now follow.

The outside surface of a balloon catheter may be coated with the coating according to the present invention and could be released immediately or in a time dependent fashion. When the balloon expands and the wall of the vessel is in contact with the balloon, the release of the o-acylated heparin can begin.

The surface of a stent may be coated with the combination of agents and the stent is implanted inside the body. The stent struts could be loaded with several layers of the agents or with just a single layer. A transporter or a vehicle to load the agents on to the surface can also be applied to the stent. The graft material of the stent graft can also be coated (in addition to the stent or as an alternative) so that the material is transported intravascularly at the site of the location of the injury.

The drug delivery catheters that are used to inject drugs and other agents intravascularly can also be used to deliver the o-acylated heparins. Other intravascular devices through which the transport can happen include atherectomy devices, filters, scaffolding devices, anastomotic clips, anastomotic bridges, suture materials etc.

The present invention envisions applying the coating directly to the intravascular implant. However, the coating can be applied to a primer, i.e. a layer or film of material upon which another coating is applied. Furthermore, the o-acylated heparins can be incorporated in a polymer matrix. Polymeric matrices (resorbable and biostable) can be used for delivery of the therapeutic agents. In some situations, when the agents are loaded on to the implant, there is a risk of quick erosion of the therapeutic agents either during the expansion process or during the phase during which the blood flow is at high shear rates at the time of implantation. In order to ensure that the therapeutic window of the agents is prolonged over-extended periods of time, polymer matrices can be used.

These polymers could be any one of the following: semitelechelic polymers for drug delivery, thermo responsive polymeric micelles for targeted drug delivery, pH or temperature sensitive polymers for drug delivery, peptide and protein based drug delivery, water insoluble drug complex drug delivery matrices polychelating amphiphilic polymers for drug delivery, bioconjugation of biodegradable poly lactic/glycolic acid for delivery, elastin mimetic protein networks for delivery, generically engineered protein domains for drug delivery, superporbus hydrogel composites for drug delivery, interpenetrating polymeric networks for drug delivery, hyaluronic acid based delivery of drugs, photocrosslinked polyanhydrides with controlled hydrolytic delivery, cytokine-incuding macromolecular glycolipids based delivery, cationic polysaccharides for topical delivery, n-halamine polymer coatings for drug delivery, dextran based coatings for drug delivery, fluorescent molecules for drug delivery, self-etching polymerization initiating primes for drug delivery, and bioactive composites based drug delivery.

One embodiment of the present invention discloses an implant, e.g., a stent for implantation into a body, e.g., blood vessel. The implant comprises a coating of O-acylated heparin or o-acylated heparin in combination with one or more compounds selected from the group consisting of (but not limited to) a polymer, fiber polymer, polyurethane, silicone rubber elastomer, drug, hydrogel, or other acceptable compound or carrier known to those of skill in the art. Methods of coating an implant such as a stent with heparin or heparin in combination with one or more of the compounds listed above, are known to those of skill in the art and are further described below and in the examples. Alternatively, O-acylated heparins of the present invention may be coated alone or in combination with the above polymer, fiber polymer, polyurethane, silicone rubber elastomer, drug, hydrogel, or other acceptable compound or carrier known to those of skill in the art onto a bypass graft. The implant, e.g., graft or stent may be used in the treatment of peripheral artery atherosclerosis disease (PAD).

Whereas the polymer of the coating may be any compatible biostable material capable of being adhered to the stent material as a thin layer, hydrophobic materials are preferred because it has been found that the release of the biologically active species can generally be more predictably controlled with such materials. Preferred materials include silicone rubber elastomers and biostable polyurethanes.

Heparin-loaded polymer can be applied by spraying or by dipping the stent graft into a solution or melt, as disclosed, for example, in U.S. Pat. Nos. 5,383,922, 5,824,048, 5,624,411 and 5,733,327. Additional methods for providing a drug-loaded polymer are disclosed in U.S. Pat. Nos. 5,637,113 and 5,766,710, where a pre-fabricated film is attached to the stent. Other methods, such as deposition via photo polymerization, plasma polymerization and the like, are also known in the art and are described in, e.g., U.S. Pat. Nos. 3,525,745, 5,609,629 and 5,824,049 and in the below examples.

U.S. Pat. No. 5,549,663 discloses a stent graft having a coating made of polyurethane fibers which are applied using conventional wet spinning techniques. Prior to the covering process, a medication is introduced into the polymer. Alternatively, a metallic stent cam be coated with a polymeric material and load the polymeric material with a drug.

Figure 23A:
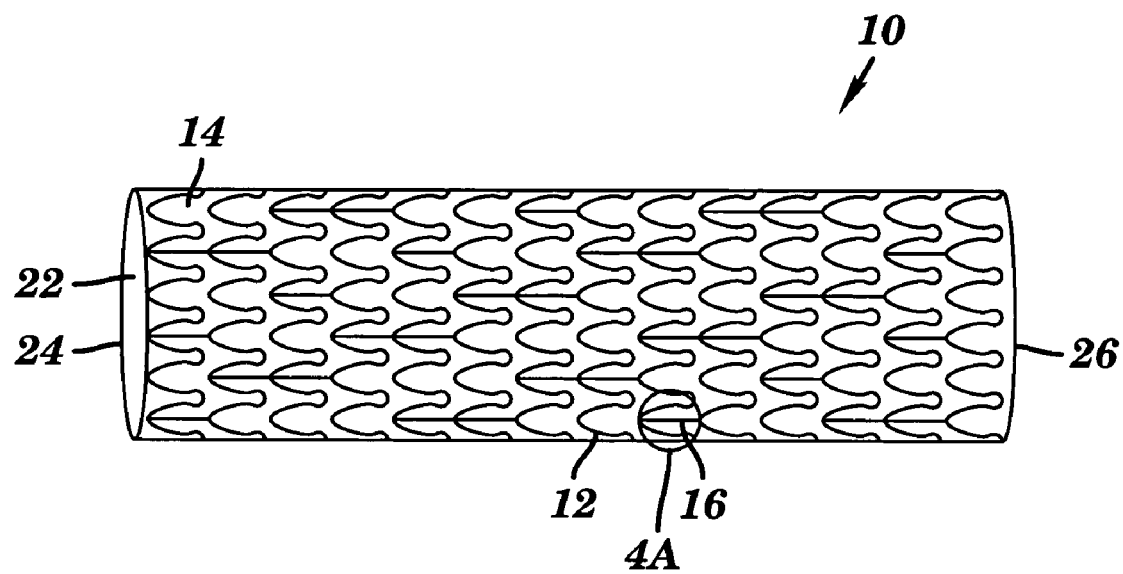
FIGS. 23A and 23B show diagrams of a stent.
Figure 23B:
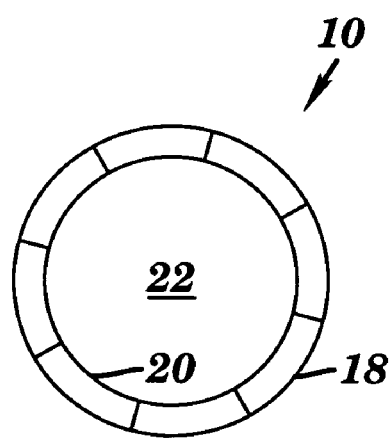

The Figures have not been drawn to scale, and the dimensions such as depth and thickness of the various regions and layers have been over or under emphasized for illustrative purposes. Referring to FIGS. 23A and 23B, a stent 10 is formed from a plurality of struts 12. Struts 12 are separated by gaps 14 and may be interconnected by connecting elements 16. Struts 12 can be connected in any suitable configuration and pattern to form an a tubular body. While a strut configuration is illustrated, any known stent configuration may be used. Stent 10 is illustrated having an outer surface or sidewall 18 (tissue-contacting surface) and an inner surface 20 (blood-contacting surface). A hollow, central bore 22 extends longitudinally from a first open end 24 to a second end 26 of stent 10.

Figure 24:
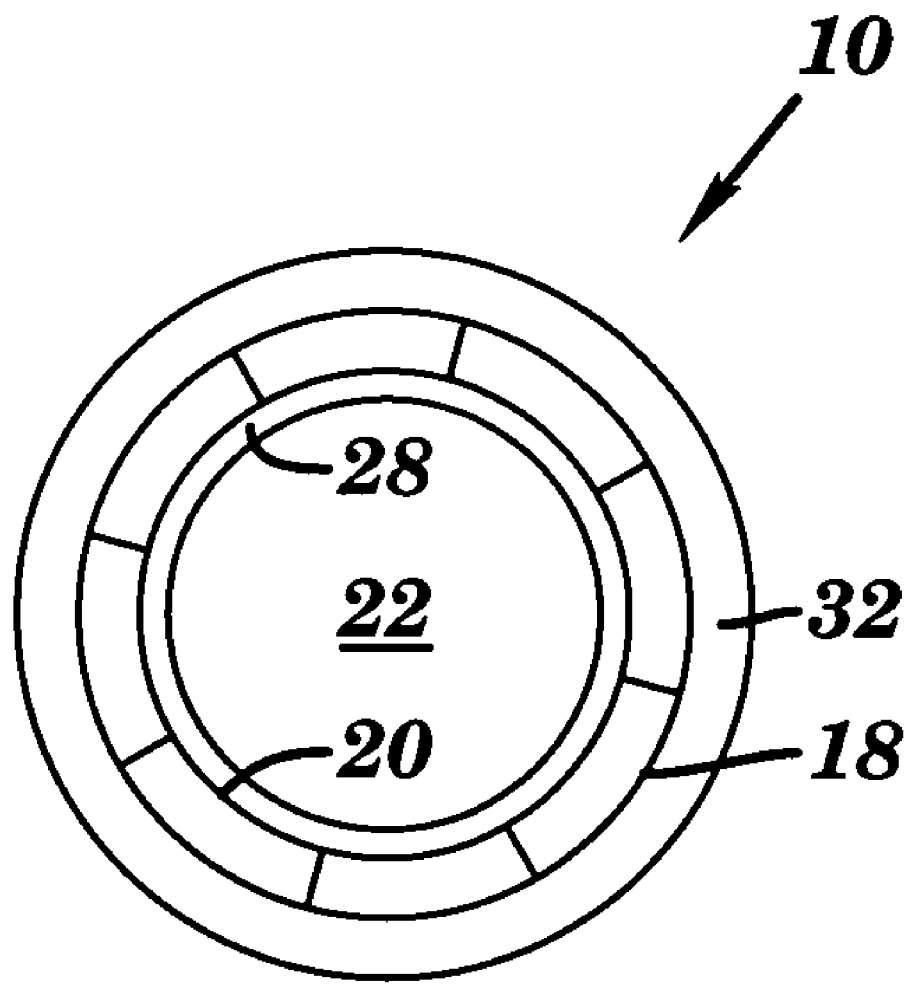
FIG. 24 shows a diagram of a stent having a second coating formed on the outer surface.

FIG. 24 illustrates stent 10 coated in accordance with the present invention. The stent may have a first coating 28 containing an O-acylated heparin on inner surface 20 and/or a second coating 32 containing an O-acylated heparin formed on outer surface 18 of stent 10. The coatings can be of any suitable thickness. The thickness of second coating 32 can be from about 0.1-15 microns, more narrowly from about 3 microns to about 8 microns. By way of example, second coating 32 can have a thickness of about 4 microns.

Cancer

In another embodiment of the present invention, methods are disclosed for the treatment and or prevention of cancer. Therapeutic amounts of O-acylated heparin, particularly O-hexanoylated heparin derivatives and O-butanoylated heparin derivatives are given to a patient alone or in combination with other cancer therapies, known to those of skill in the art. Compounds may be administered before, at the same time as, or after the administration of other conventional cancer therapies. O-acylated heparins of the present invention may be given prior to the diagnosis of cancer, such as in the case of a patient having a high-risk of developing cancer, or after the successful treatment of cancer (ie. remission). The compounds of the present invention may also be administered with the goal of reducing metastases.

Examples of tumors which may be inhibited, but are not limited to, lung cancer (e.g. adenocarcinoma, small cell, and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

For the treatment of the above conditions, the compound of the invention may be advantageously employed in combination with one or more other medicinal agents such as anti-cancer agents.

For example, O-acylated heparins of the invention may be given in combination with one or more compounds selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and antitumor podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene, or aromatase inhibitors such as exemestane, anastrozole, letrazole and vorozole.

Aberrant Smooth Muscle Cell Proliferation

The methods of the present invention can be used to treat disorders wherein smooth muscle cells abnormally proliferate. Such conditions include, but are not limited to, restenosis (following angioplasty, vascular stent placement, coronary artery stent placement, peripheral artery stent placement, or cerebral artery stent placement), pulmonary hypertension, and pulmonary fibrosis. We have shown that heparin can inhibit fibroblast proliferation (Dahlberg et al. Am Rev. Respir. Dis. 143:A357, 1993) and can inhibit pulmonary fibrosis in the rat in response to bleomycin. We also have unpublished data showing hexanoylated and butanoylated heparins, which have virtually no anticoagulant property, can also inhibit fibroblast proliferation and thus may offer a potent therapeutic agent for human pulmonary fibrosis.

The methods of the invention provide for the treatment (reduction or cessation) or prevention of disorders wherein smooth muscle cells are abnormally proliferating. These methods include the administration of O-acylated heparin compounds, preferably O-hexanoylated or O-butanoylated heparin derivatives.

Administration of the compounds of the invention to treat and/or prevent aberrant smooth muscle cell proliferation are known to those skilled in the art and are presented above.

Preferably, O-acylated heparin is coated on an implantable stent, wherein the delivery of the heparin is controlled and sufficient to reduce or ablate aberrant smooth muscle cell proliferation.

Pulmonary Hypertension and Pulmonary Fibrosis

In yet another embodiment, the present invention is directed to the treatment and/or prevention of pulmonary hypertension and pulmonary fibrosis. Preferably, O-acylated heparins of the invention are presented for administration to the respiratory tract as a snuff or an aerosol or solution for a nebulizer, or as a microfine powder for insufflation, alone or in combination with an inert carrier such as lactose. In such a case the particles of the active compound suitably have diameters of less than 50 microns, preferably less than 10 microns, more preferably between 2 and 5 microns. The methods of the present invention are directed to the treatment of both primary and secondary pulmonary hypertension and pulmonary fibrosis.

EXAMPLES

Preparation of O-Acylated Heparins

In this example, we describe the synthesis of Low Molecular Weight (LMW) heparin by periodate oxidation, its characterization, and its O-acylation.

Heparin was fragmented by periodate oxidation based on a modification of an earlier procedure (described in U.S. Pat. No. 4,990,502), wherein heparin sodium salt (20 g, 1.43 mmol) was dissolved in 175 mL distilled water. The pH was adjusted to 5.0 using 1 N HCl. $NaIO_4$ (15 g, 0.070 mol), dissolved in 500 ML water, was added in a single portion with stirring. The pH was readjusted to 5.0 using 1 N HCl and left for 24 hours at 4° C. in the dark. The solution was dialyzed against 4 volumes of water (with one change of water) for 15 h at 4° C.

To the approximately 1.5 L solution obtained after dialysis, 32 mL of 10 N NaOH was added. The solution was stirred at room temperature for 3 h. To prevent the development of colored products, this step was done in the dark.

$NaBH_4$ (1 g, 0.026 mol) was added in one portion and the approximately 1.5 L of solution was stirred for 4 hours. The pH was then adjusted to 4.0 using 37% HCl and the solution was stirred for an additional 15 min. The solution was neutralized to pH 7.0 using 1 N NaOH, NaCl (32.8 g, 0.56 mol) followed by 2.54 L of ethanol. The solution was left for 3 h without stirring and the precipitate was recovered by centrifugation at 15000 rpm (22,000×g) for 20 min. The precipitate was recovered by decantation and suspended in 400 mL absolute ethanol. The solution was filtered using a Buchner funnel and left to dry for 5 hours under vacuum affording 14.2 g of product.

Figure 1:
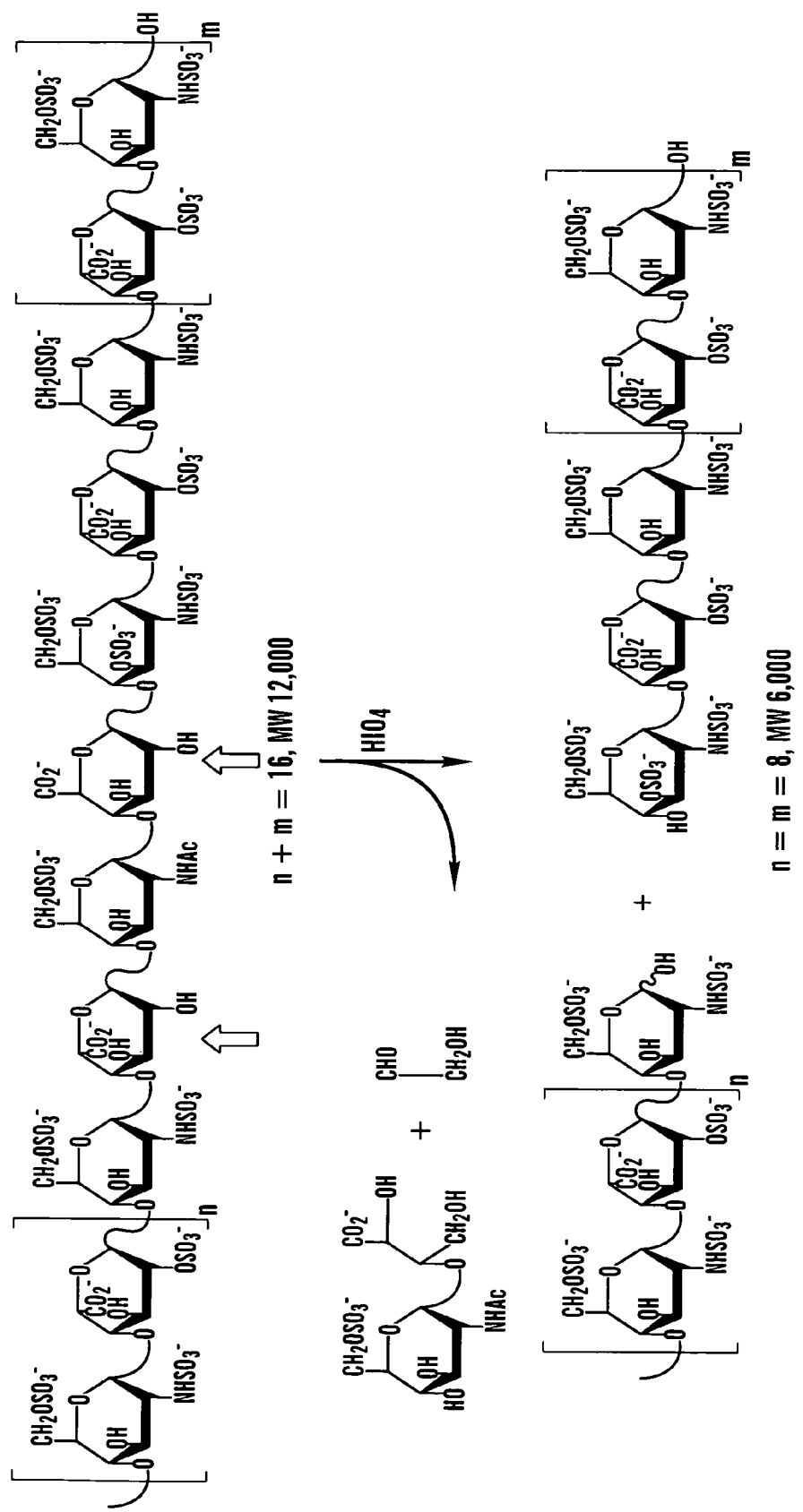
FIG. 1 shows the preparation of O-acylated heparin derivatives.

The product was dissolved in 190 mL of water. NaCl (2.8 g, 0.05 mol) was added and the pH was adjusted to 3.5 using 1 N HCl. The volume was adjusted to 280 mL using water. Absolute ethanol (240 mL) was added with stirring. The solution was stirred 15 min and then left without stirring for 10 hours at room temperature. After decanting, the precipitate was recovered and dissolved in water. The ethanol was removed by rotary evaporation under reduced pressure and freeze-dried affording ~10 g of LMW heparin fragments (FIG. 1).

NMR Sample Preparation

Figure 2:
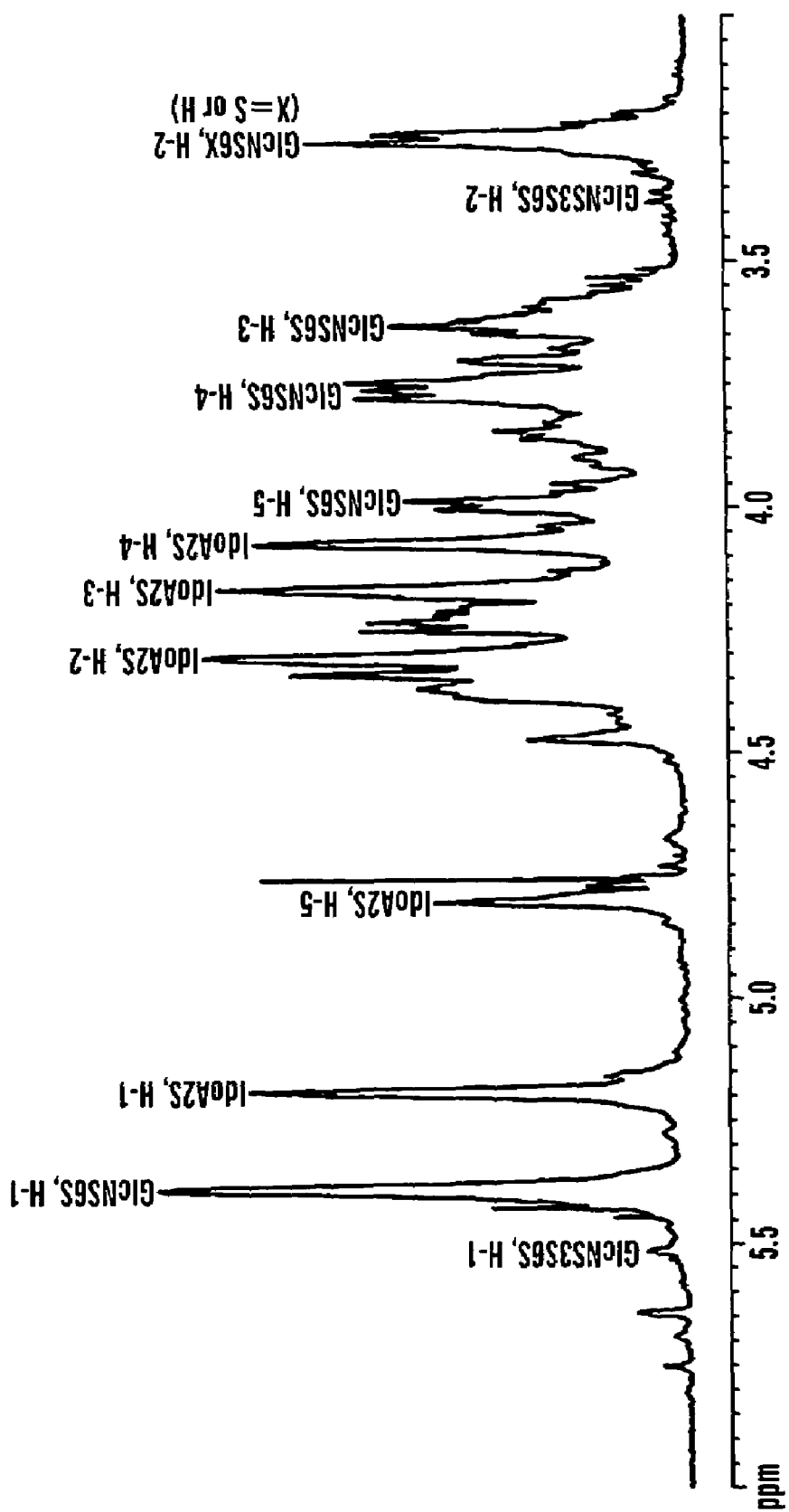
FIG. 2 shows the results of $^1H$ NMR spectroscopy, where approximately 10 mg of each sample was exchanged by lyophilization three times from 0.5 ml portions of 99.9% $^2H_2O$ before being redissolved in $^2H_2O$ for NMR analysis. Chemical shifts are reported relative to TMS at 0.00 ppm. The degree of substitution (O-acylation) was determined from the ratio of the integrated area of the peaks assigned to the aliphatic methyl protons of the hexanoyl group (0.753 ppm) to the anomeric proton of IdoA2S (5.092 ppm).

For $^1H$ NMR spectroscopy, approximately 10 mg of each sample was exchanged by lyophilization three times from 0.5 ml portions of 99.9% $^2H_2O$ before being redissolved in $^2H_2O$ for NMR analysis. Chemical shifts are reported relative to TMS at 0.00 ppm. The degree of substitution (O-acylation) was determined from the ratio of the integrated area of the peaks assigned to the aliphatic methyl protons of the hexanoyl group (0.753 ppm) to the anomeric proton of IdoA2S (5.092 ppm) (Table 1, FIG. 2).

Gradient PAGE Analysis

Gradient polyacrylamide gel electrophoresis (PAGE) was performed on a 32 cm vertical slab gel unit PROTEAN II equipped with Model 1000 power source from Bio-Rad IRichmond, Calif.). Polyacrylamide linear gradient resolving gels (14×28 cm), 12-22%) total acrylamide) were prepared and run as previously described (Edens et al., 1992, J. Pharm. Sci. 81, 823-827). The molecular sizes of the oligosaccharide samples were determined by comparing with a banding ladder of heparin oligosaccharide standards prepared from bovine lung heparin. Oligosaccharides were visualized by Alcian blue staining. The average MW of the product was determined to be 6,000.

Anti-factor Xa and anti-factor IIa activities

LMW heparin and heparin standard were in diluted normal human plasma. Chromogenic Xa substrate S-2732 (Suc-I1c-Glu(gamma-piperidyl)-Gly-Arg-pNA) 2.9 MM in 50 mM Tris, 7.5 µM EDTA, pH 8.4 buffer (200 µL), was added to 25 µL of plasma containing sample and 200 µL of bovine Factor Xa (1.25/mL). After mixing, the reaction was incubated for 8 min. at 37 degrees Celsius and 200 µL of 20% aqueous acetic was added. Residual Factor Xa was then determined by measuring absorbance at 405 nm. Anti-factor IIa activity was determined by incubating 50 ML of LMW heparin in NHP diluted 4-fold with water with 50 mL of human thrombin (12 NIH units/mL) at 37° C. for 30 s. then 50 mL of (2.5 mmol/mL of Chromogenic TH (ethylmalonyl-Pro-Aeg-p-nitroanilide hydrochloride) was added, and the amidolytic thrombin activity was measured at 405 nm. Measurements were performed on an ACL 300 plus from Instrumentation (Lexington, Mass.) and calculated in comparison with USP Heparin Reference Standard (K-3) supplied by U.S. Pharmacopeial Convention (Rockville, Md.). The product exhibited no measurable anti-factor Xa or anti-factor IIa activity.

O-acylated LMW Heparin Derivatives (1) O-Hexanoyl derivative of periodate-oxidized heparin fragments. These were obtained by treating the tributylaminmonium salt of periodate oxidized heparin fragments with hexanoic anhydride as described previously (Gohda et al., 2001, Biomacromolecules, 2(4):1178-83)(Lormeau U.S. Pat. No. 4,990,502). Briefly, the tributylammonium salt (11.9 g) was dissolved in dry DMF (114 mL), kept under Ar and cooled to 0 degrees Celsius. 4-Dimethylaminopyridine (0.695 g, 5.69 mmol), hexanoic anhydride (26.2 mL, 0.113 mol), and tributylamine (227 mL, 0.113 mol) were successively added in single portions, and the reaction was allowed to proceed under argon at room temperature for 24 hours. After cooling to 0° C., 5% NaHCO3 in water (227 mL) was gradually added and the solution was stirred at room temperature for 48 h. Excess NaHCO3 was eliminated by slow, dropwise addition of 1 N HCL (~200 mL) until pH4 was reached and then readjusted to pH 7 with 1 N NaOH (~150 mL). Cold denatured (95%) ethanol (5L, 5 vol) was added with stirring. The sample was allowed to sit overnight at 4 degrees Celsius to afford precipitate. The precipitate was recovered by by decanting and dissolved in 0.2 M NaCl (114 mL), and the precipitation procedure was repeated by adding absolute ethanol (570 mL). The precipitate was recovered by centrifugation at 15000 rpm for 20 minutes, dissolved in water (114 mL), and passed through a column (300 mL) of Dowez 50WX8($H^+$) cation-exchange resine and 600 ml was recovered. The acid was neutralized to pH 7 with 10 N NaOH and the solution was filtered through a 0.22 µm Millipore filter. After lyophilization, O-hexanoyl heparin oligosaccharides (7.12 g) was obtained as an off-white powder (FIG. 3).

O-butanoylated LMW Heparin

This derivative was prepared from the tributylaminmonium salt of LMW heparin by treatment with butyric anhydride under the same condition as described for hexanoyl derivative (see above).

Application of Heparin to Stent

O-acylated heparin derivatives can be coated on stents using the methods set forth in U.S. Pat. No. 6,620,194. The method is generally as follows.

The application of the coating material to the stent is quite similar for all of the materials and the same for the heparin and one or more additional suspensions prepared as in the above Examples. The suspension to be applied is transferred to an application device, typically a paint jar attached to an air brush, such as a Badger Model 150, supplied with a source of pressurized air through a regulator (Norgren, 0-160 psi). Once the brush hose is attached to the source of compressed air downstream of the regulator, the air is applied. The pressure is adjusted to approximately 15-25 psi and the nozzle condition checked by depressing the trigger.

Any appropriate method can be used to secure the stent for spraying and rotating fixtures. Both ends of the relaxed stent can be fastened to the fixture by two resilient retainers, commonly alligator clips, with the distance between the clips adjusted so that the stent remains in a relaxed, unstretched condition. The rotor is then energized and the spin speed adjusted to the desired coating speed, nominally about 40 rpm.

With the stent rotating in a substantially horizontal plane, the spray nozzle is adjusted so that the distance from the nozzle to the stent is about 2-4 inches and the composition is sprayed substantially horizontally with the brush being directed along the stent from the distal end of the stent to the proximal end and then from the proximal end to the distal end in a sweeping motion at a speed such that one spray cycle occurs in about three stent rotations. Typically a pause of less than one minute, normally about one-half minute, elapses between layers. Of course, the number of coating layers will vary with the particular application. For example, for a coating level of 3-4 mg of heparin per cm.sup.2 of projected area, 20 cycles of coating application should be required and about 30 ml of solution will be consumed for a 3.5 mm diameter by 14.5 cm long stent.

The rotation speed of the motor, of course, can be adjusted as can the viscosity of the composition and the flow rate of the spray nozzle as desired to modify the layered structure. Generally, with the above mixes, the best results will be obtained at rotational speeds in the range of 30-50 rpm and with a spray nozzle flow rate in the range of 4-10 ml of coating composition per minute, depending on the stent size. It is contemplated that a more sophisticated, computer-controlled coating apparatus will successfully automate the process demonstrated as feasible in the laboratory.

The coated stent can be thereafter subjected to a curing step in which the pre-polymer and crosslinking agents cooperate to produce a cured polymer matrix containing the biologically active species. The curing process involves evaporation of the solvent xylene, THF, etc. and the curing and crosslinking of the polymer. Certain silicone materials can be cured at relatively low temperatures, (i.e. RT-50° C.) in what is known as a room temperature vulcanization (RTV) process. More typically, however, the curing process involves higher temperature curing materials and the coated stents are put into an oven at approximately 90° C. or higher for approximately 16 hours. The temperature may be raised to as high as 150° C. for dexamethasone containing coated stents. Of course, the time and temperature may vary with particular silicones, crosslinkers, and biologically active species.

Stents coated and cured in the manner described need to be sterilized prior to packaging for future implantation. For sterilization, gamma radiation is a preferred method particularly for heparin containing coatings; however, it is possible that stents coated and cured according to the process of the invention subjected to gamma sterilization may be too slow to recover their original posture when delivered to a vascular or other lumen site using a catheter unless a pretreatment step as at 24 is first applied to the coated, cured stent.

The pretreatment step can involve an argon plasma treatment of the coated, cured stent in the unconstrained configuration. In accordance with this procedure, the stents are placed in a chamber of a plasma surface treatment system such as a Plasma Science 350 (Himont/Plasma Science, Foster City, Calif.). The system is equipped with a reactor chamber and RF solid-state generator operating at 13.56 mHz and from 0-500 watts power output and being equipped with a microprocessor controlled system and a complete vacuum pump package. The reaction chamber contains an unimpeded work volume of 16.75 inches (42.55 cm) by 13.5 inches (34.3 cm) by 17.5 inches (44.45 cm) in depth.

In the plasma process, unconstrained coated stents are placed in a reactor chamber and the system is purged with nitrogen and a vacuum applied to 20-50 mTorr. Thereafter, inert gas (argon, helium or mixture of them) is admitted to the reaction chamber for the plasma treatment. A highly preferred method of operation consists of using argon gas, operating at a power range from 200 to 400 watts, a flow rate of 150-650 standard ml per minute, which is equivalent to 100-450 mTorr, and an exposure time from 30 seconds to about 5 minutes. The stents can be removed immediately after the plasma treatment or remain in the argon atmosphere for an additional period of time, typically five minutes.

After this, the stents can be exposed to gamma sterilization at 2.5-3.5 Mrad. The radiation may be carried out with the stent in either the radially non-constrained status—or in the radially constrained status.

With respect to the anticoagulant material heparin, the percentage in the tie layer is nominally from about 20-50% and that of the top layer from about 0-30% active material. The coating thickness ratio of the top layer to the tie layer varies from about 1:10 to 1:2 and is preferably in the range of from about 1:6 to 1:3.

Suppressing the burst effect also enables a reduction in the drug loading or in other words, allows a reduction in the coating thickness, since the physician will give a bolus injection of antiplatelet/anticoagulation drugs to the patient during the stenting process. As a result, the drug imbedded in the stent can be fully used without waste. Tailoring the first day release, but maximizing second day and third day release at the thinnest possible coating configuration will reduce the acute or subacute thrombosis.

Results

Figure 4:
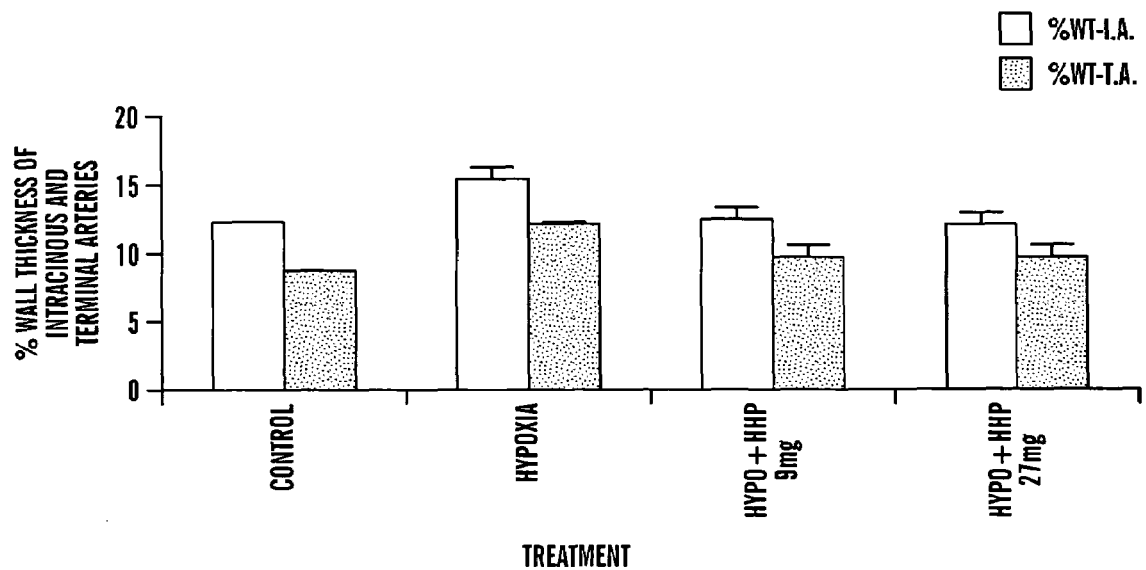
FIG. 4 shows that hexanoylated heparin (HHP) significantly inhibited pulmonary artery smooth muscle cell proliferation in vivo.
Figure 5:
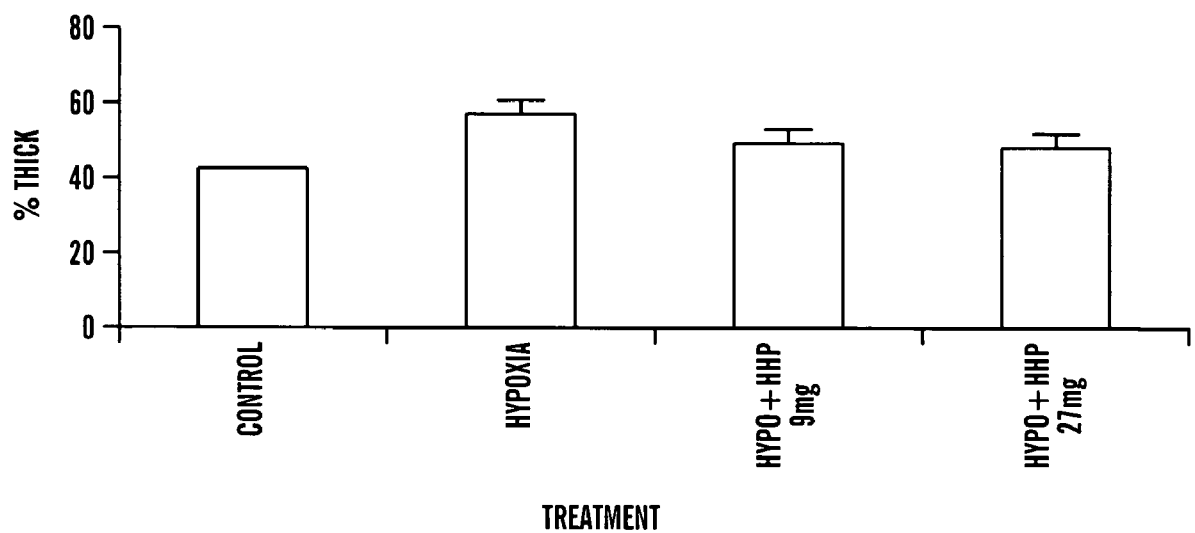
FIG. 5 shows that hexanoylated heparin (HHP) significantly inhibited the development of pulmonary hypertension induced by hypoxia in the pig lung.
Figure 6:
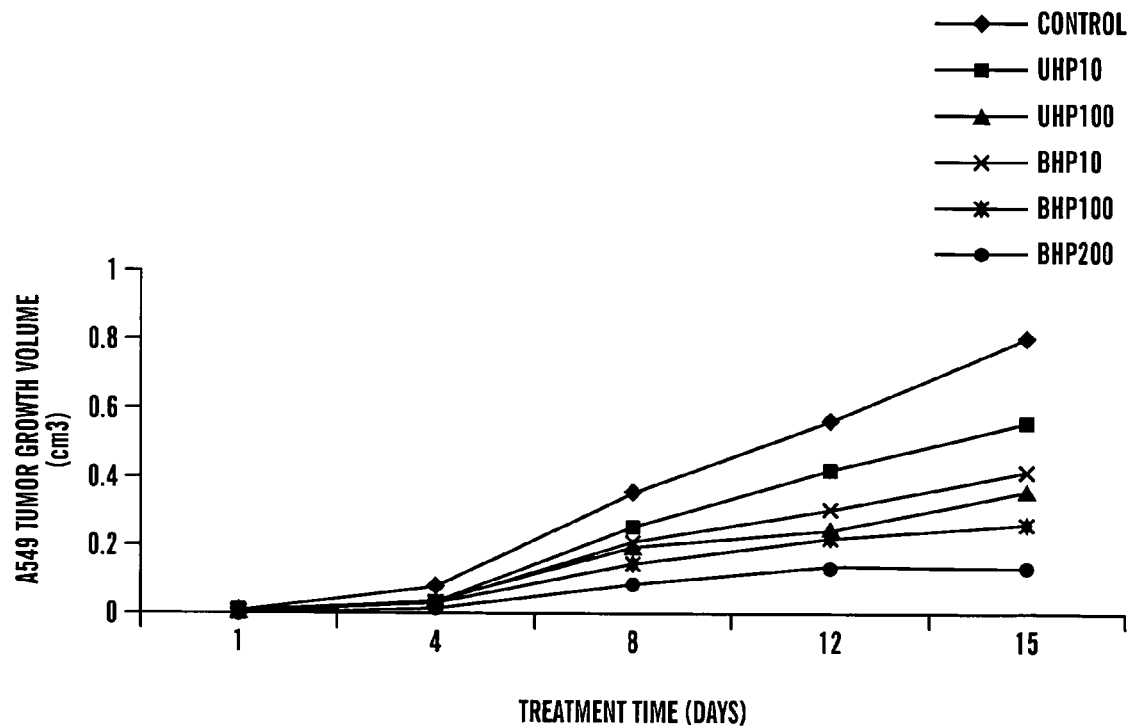
FIG. 6 shows a comparison of tumor growth in SCID mice treated with various doses of native heparin (UHP) and butanoylated heparin (BHP). Butanoylated heparin significantly inhibited A549 (non-small cell lung carcinoma) cell tumor growth in a dose dependent manner.
Figure 7:
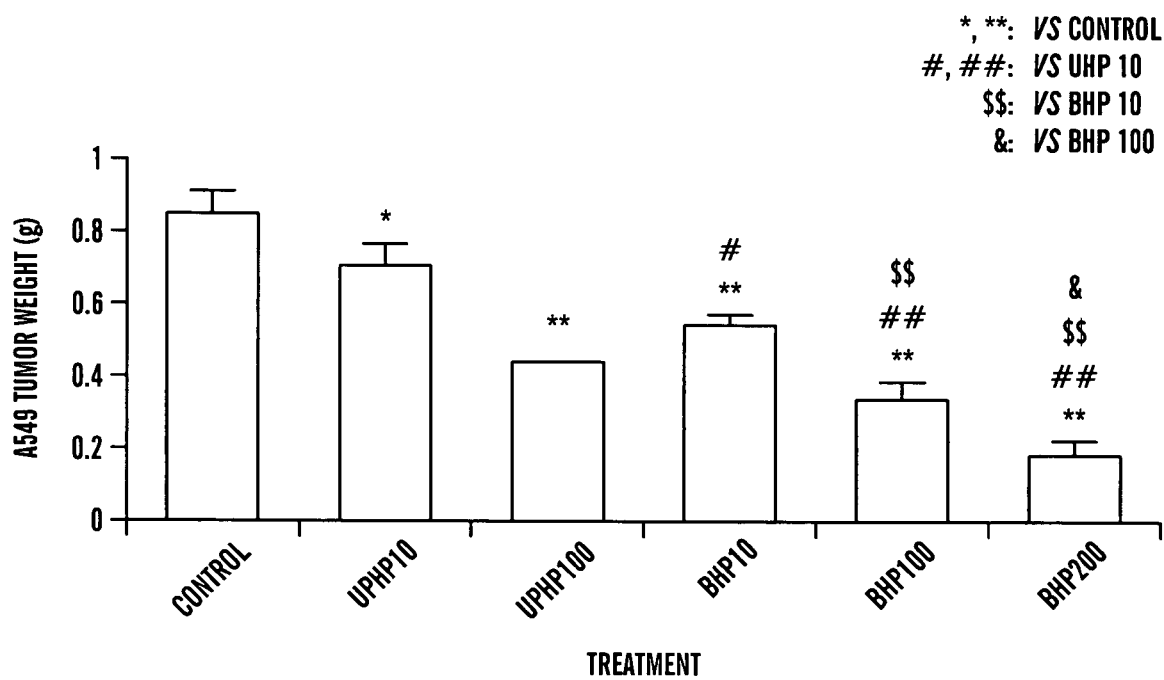
FIG. 7 shows a comparison of tumor weights from SCID mice treated with native heparin and butanoylated heparin. Butanoylated heparin (BHP) significantly decreased A549 (non-small cell lung carcinoma) cell tumor weight in a dose dependent manner.
Figure 8:
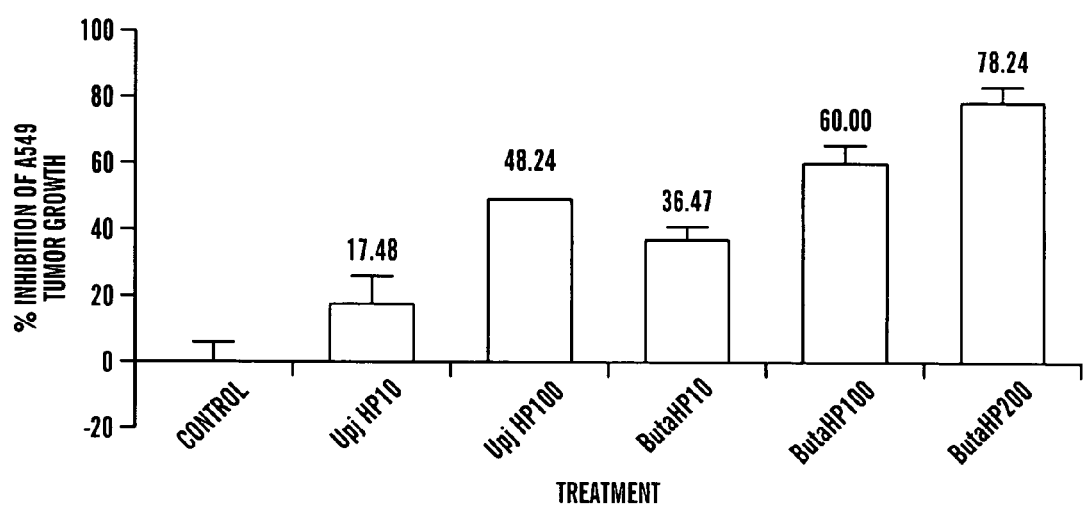
FIG. 8 shows percent inhibition of tumor growth in SCID mice treated with native heparin and butanoylated heparin. Butanoylated heparin (BHP) significantly inhibited A549 (non-small cell lung carcinoma) cell tumor growth in a dose dependent manner.
Figure 9:
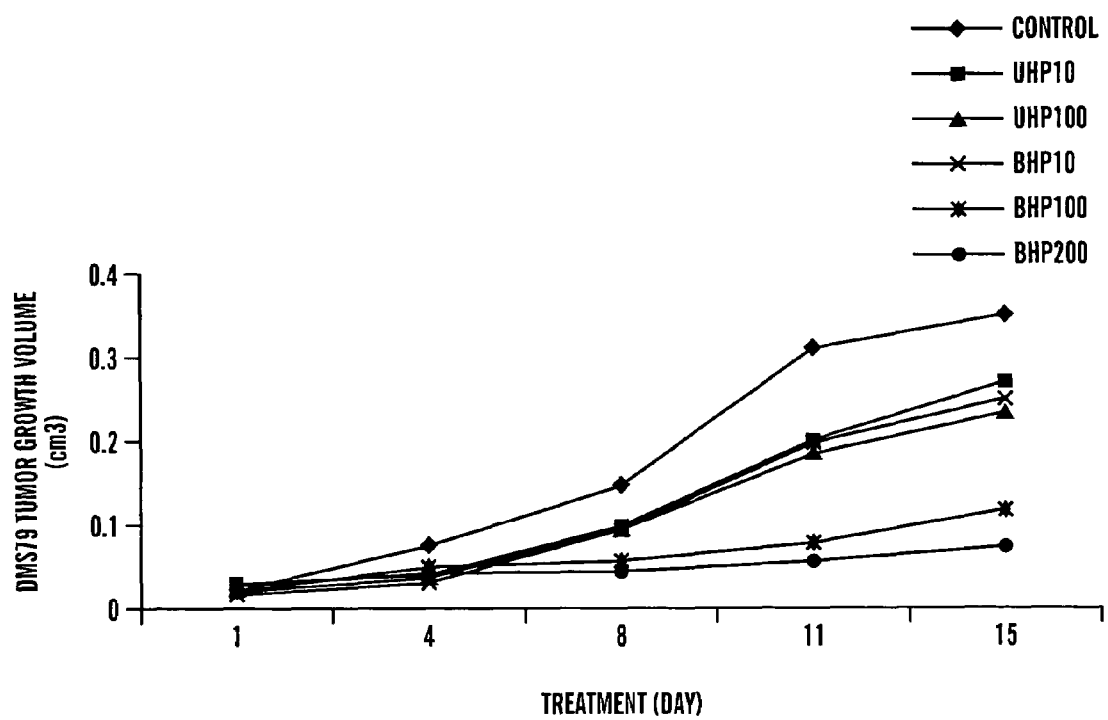
FIG. 9 shows tumor growth in SCID mice treated with native heparin and butanoylated heparin. Butanoylated heparin (BHP) significantly inhibited DMS79 (small cell lung carcinoma) cell tumor growth in a dose dependent manner.
Figure 10:
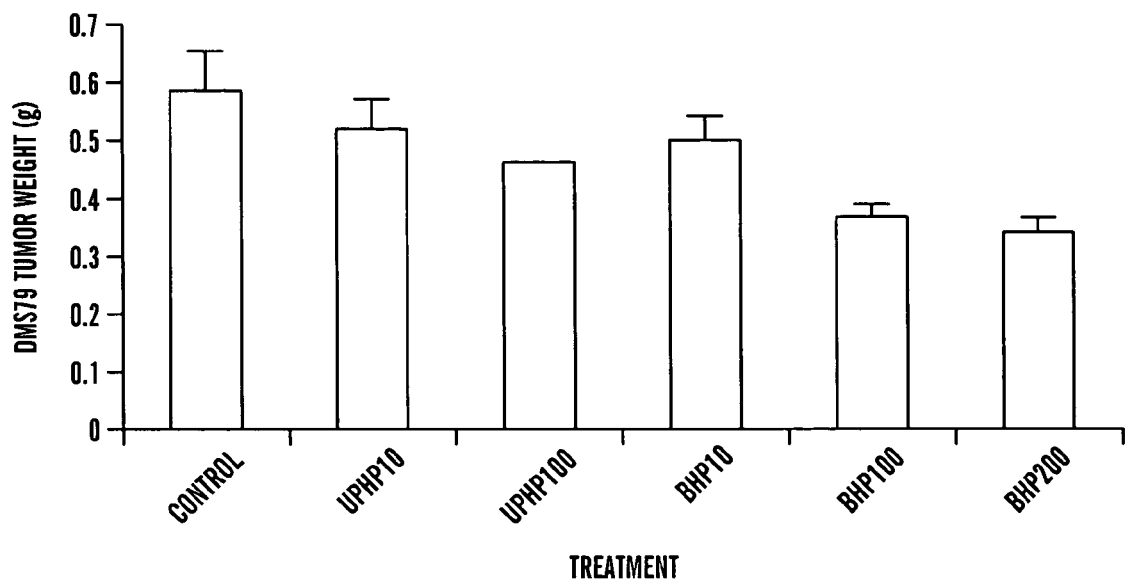
FIG. 10 shows tumor weight from SCID mice treated with native heparin and butanoylated heparin. Butanoylated heparin (BHP) significantly decreased DMS79 (small cell lung carcinoma) cell tumor weight in a dose dependent manner.

Effect on smooth muscle cell proliferation in vitro and in vivo. Hexanoylated LMW heparin significantly inhibited pulmonary artery smooth muscle cell proliferation in vivo (FIG. 4) and the development of pulmonary hypertension induced by hypoxia in pig lung (FIG. 5)

In comparison to non-acylated heparin fragments, hexanoylated LMW heparin significantly enhanced the antiproliferative effect of bovine pulmonary artery smooth muscle cells in vitro.

Figure 11:
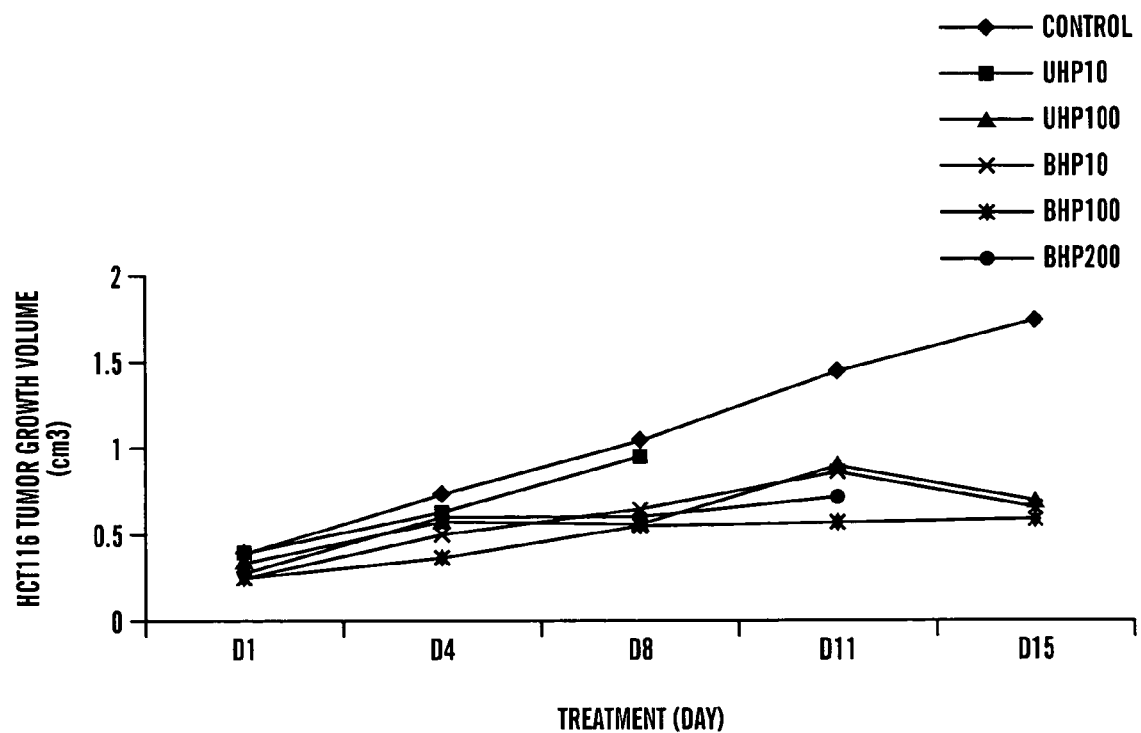
FIG. 11 shows tumor growth in SCID mice treated with native heparin and butanoylated heparin. Butanoylated heparin (BHP) significantly inhibited HCT116 (colon cancer) cell tumor growth in a dose dependent manner.
Figure 12:
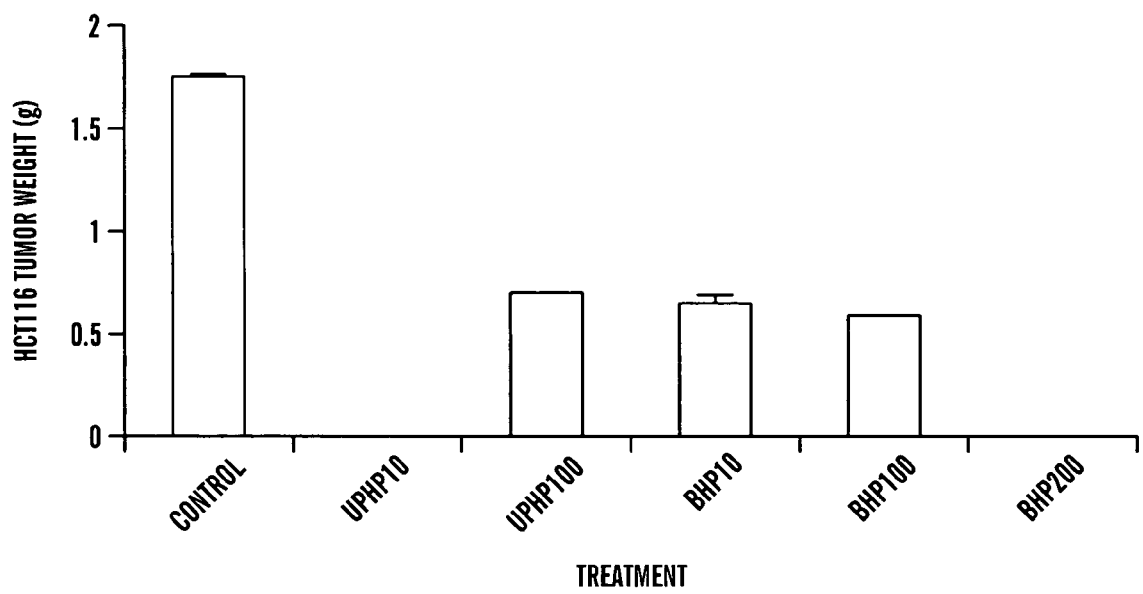
FIG. 12 shows tumor growth in SCID mice treated with native heparin and butanoylated heparin. Butanoylated heparin (BHP) significantly inhibited HCT116 (colon cancer) cell tumor growth in a dose dependent manner.

Effect of O-acylation of heparin on tumor growth in vivo. As seen in FIGS. 6-10, butanoylated heparin significantly inhibited the growth of both A549 non-small cell lung carcinoma and DMS79 small cell lung carcinoma in SCID mice (FIG. 6-10). In addition, FIGS. 11 and 12 demonstrate that butanoylated heparin significantly inhibited the growth of HCT116 colonic carcinoma in SCID mice.

Figure 13:
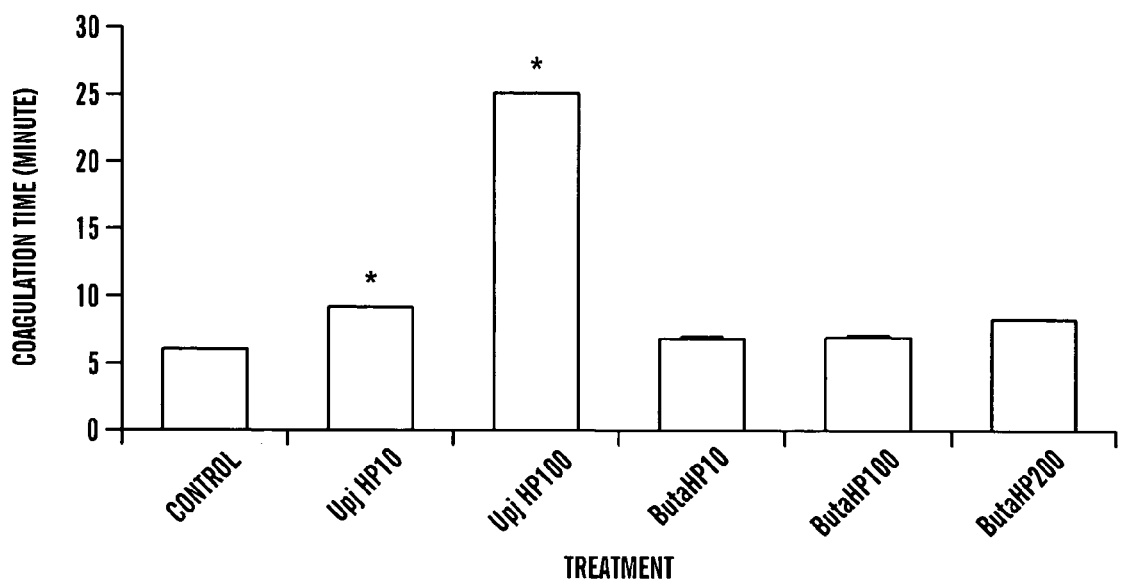
FIG. 13 shows coagulation time for various heparin compounds. Native heparin (UPJ HP) increased coagulation time in a dose dependent manner. Butanoylated heparin had no significant effect on coagulation time.
Figure 14:
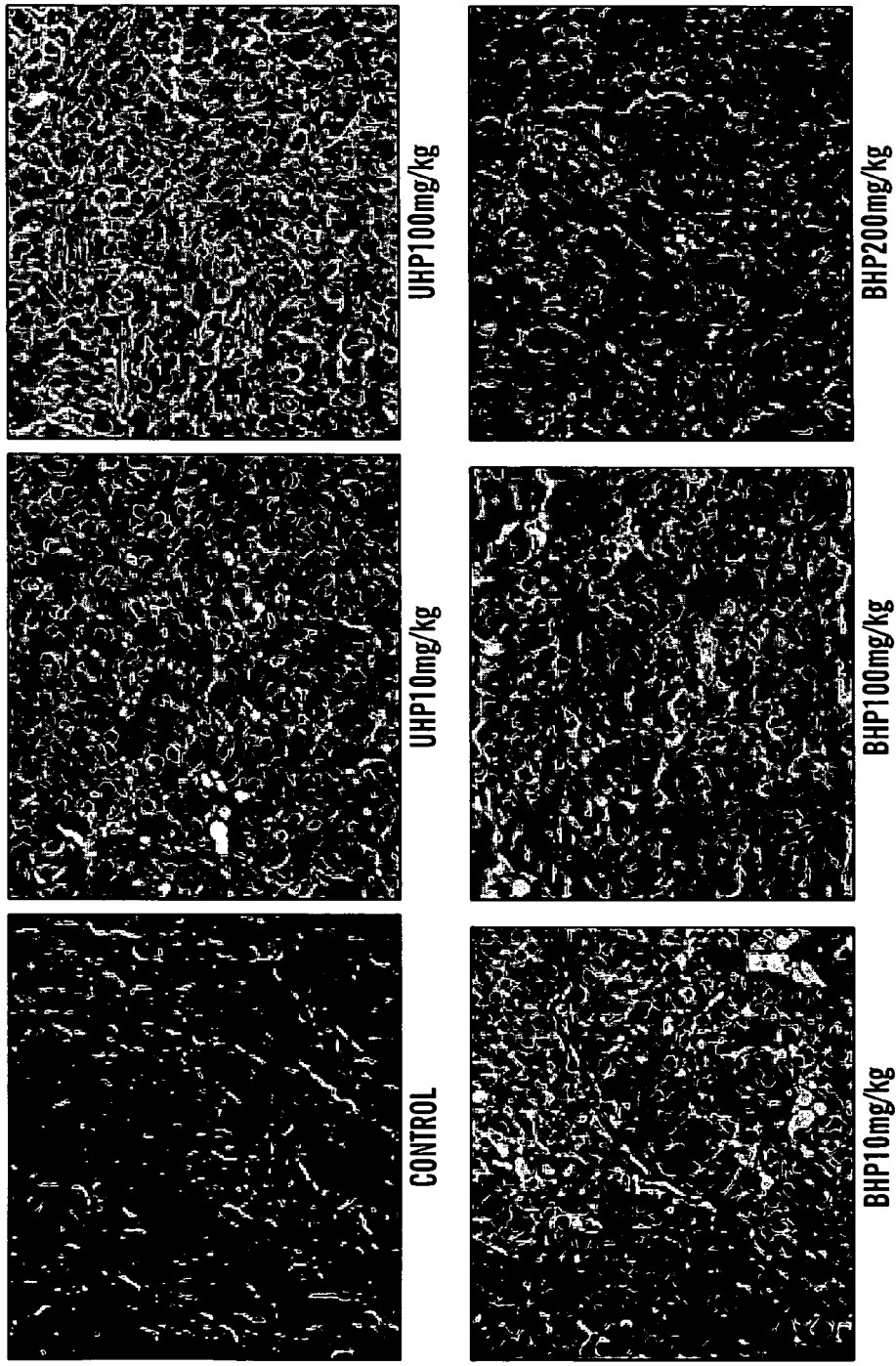
FIG. 14 shows histology of A549 cell tumor tissue grown in SCID mice. Hemorrhage was detected in mice treated with 100 mg/kg native, unfractionated heparin only.
Figure 15:
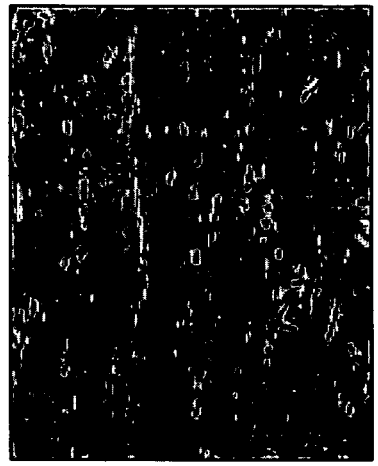
FIG. 15 shows histology of heart from SCID mice bearing A549 cell tumor. No significant pathological change was observed in any group.
Figure 15:
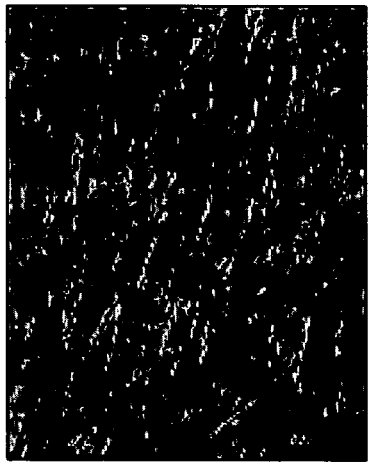
Figure 15:
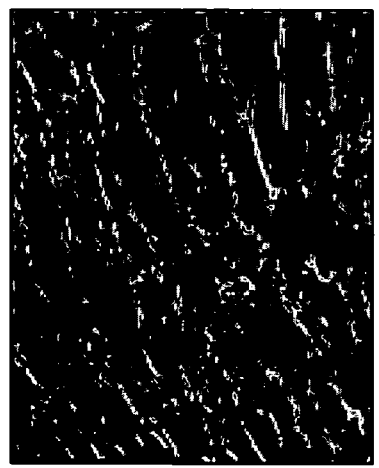
Figure 15:
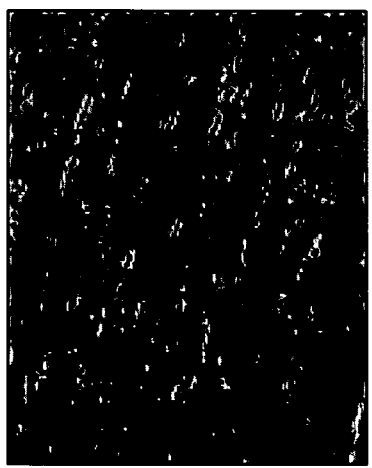
Figure 15:
Figure 15:
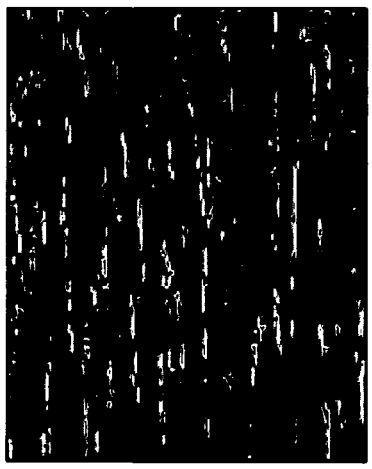
Figure 16:
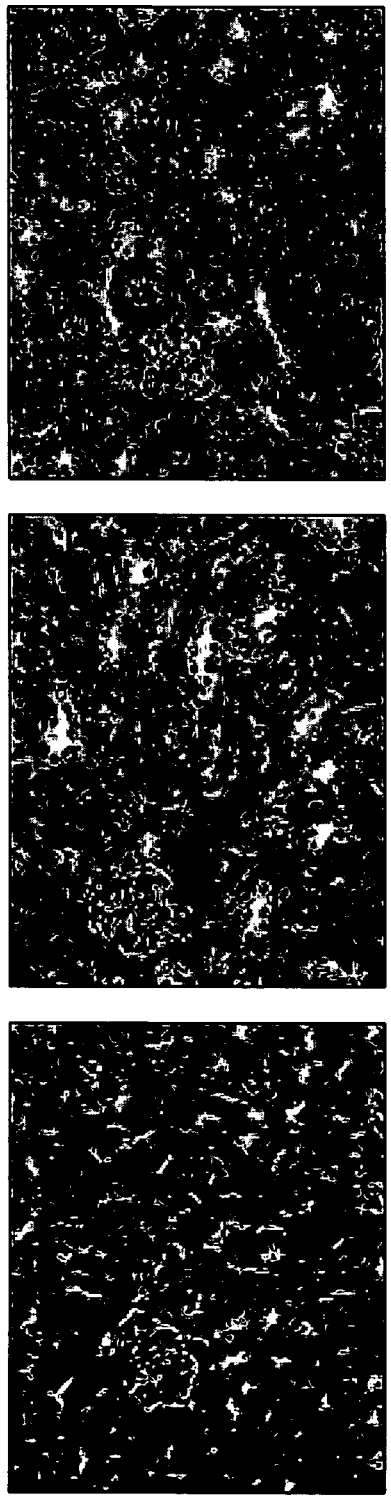
FIG. 16 shows histology of kidney from SCID mice bearing A549 cell tumor. No significant pathological change was observed in any group.
Figure 16:
Figure 17:
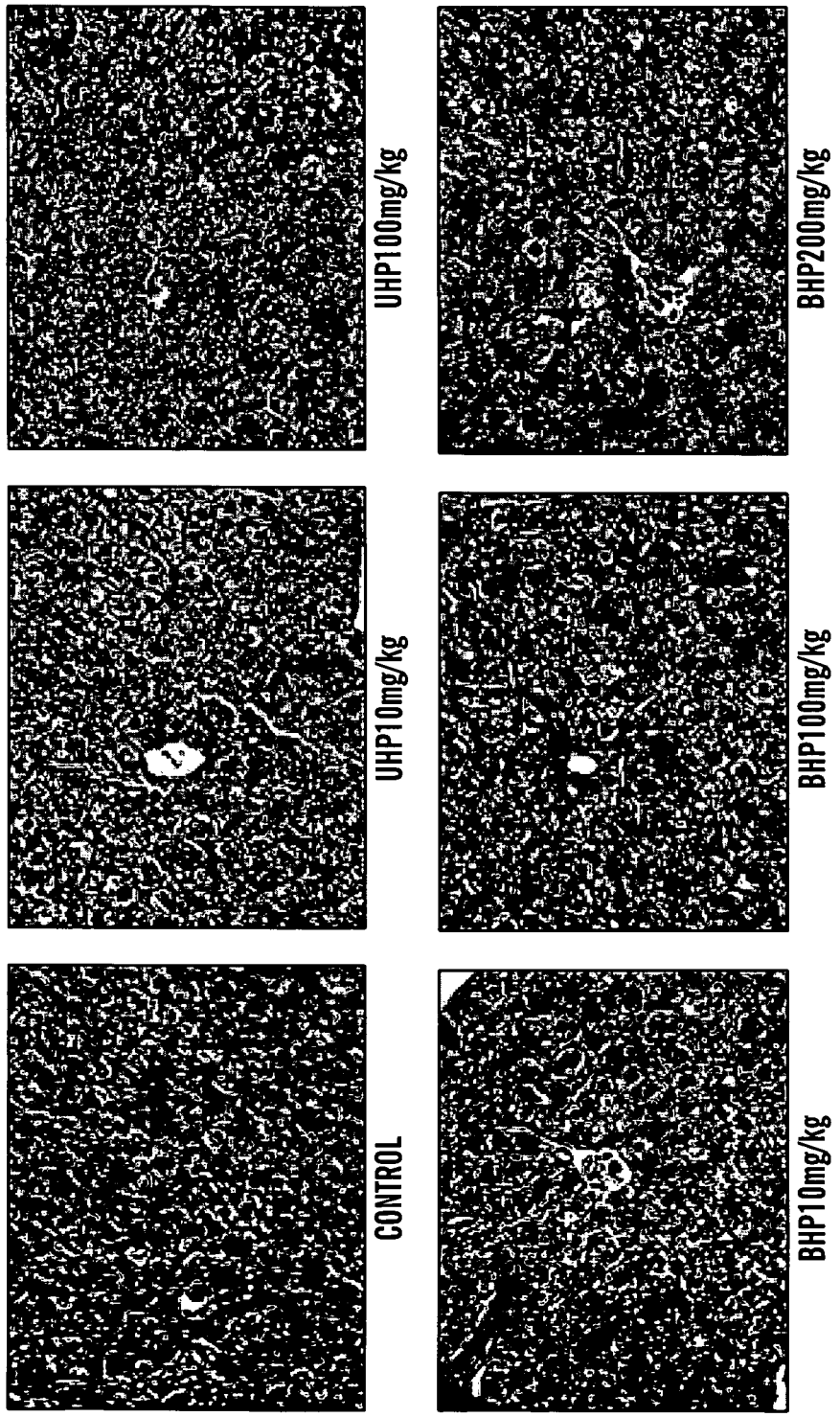
FIG. 17 shows histology of liver from SCID mice bearing A549 cell tumor. No significant pathological change was observed in any group.
Figure 18:
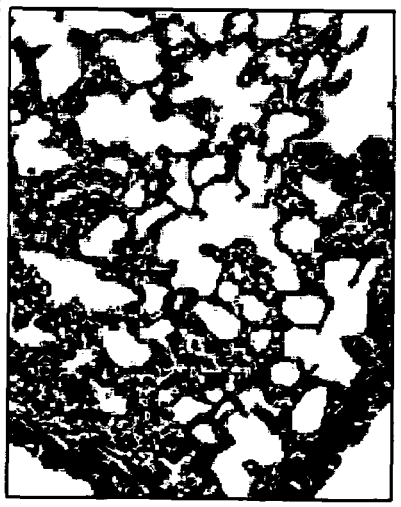
FIG. 18 shows histology of lung from SCID mice bearing A549 cell tumor. No significant pathological change was observed in any group.
Figure 18:
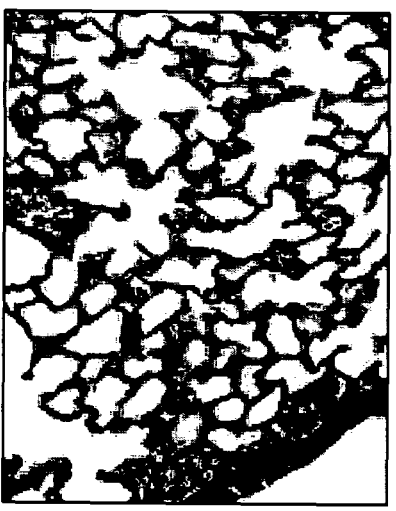
Figure 18:
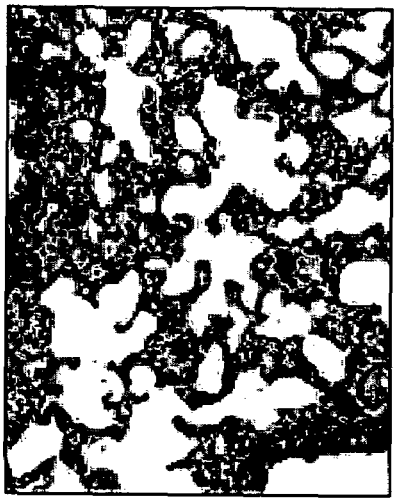
Figure 18:
Figure 18:
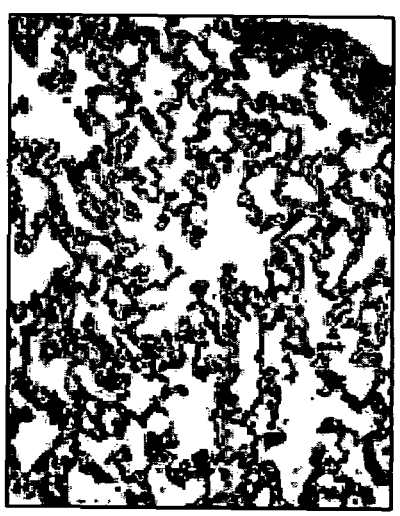
Figure 18:
Figure 19:
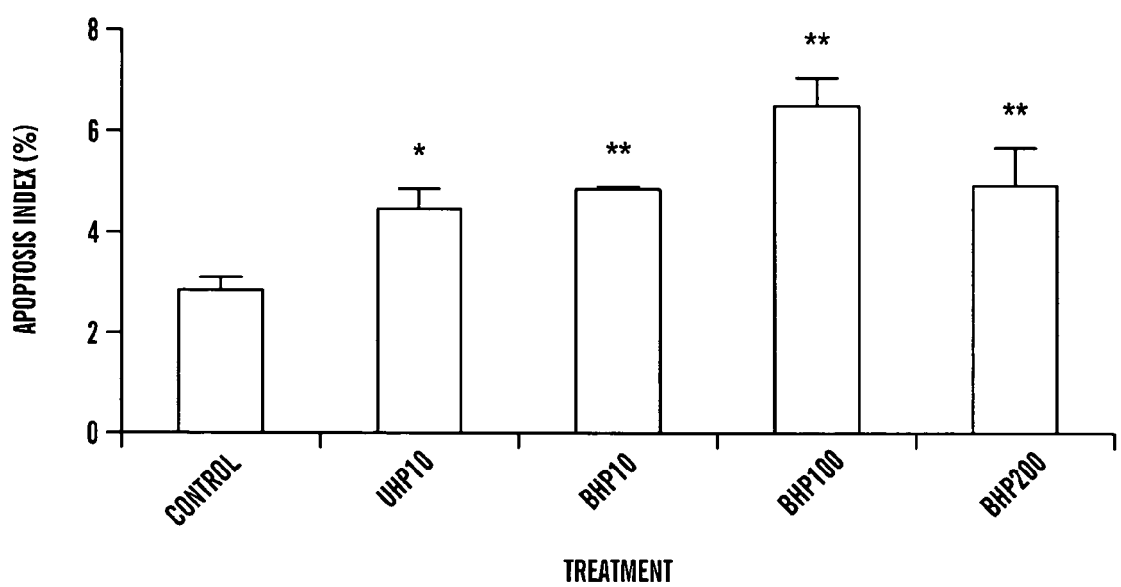
FIG. 19 shows apoptosis index in different treatment groups. Heparin significantly induces apoptosis in tumor grown in SCID mice.
Figure 20:
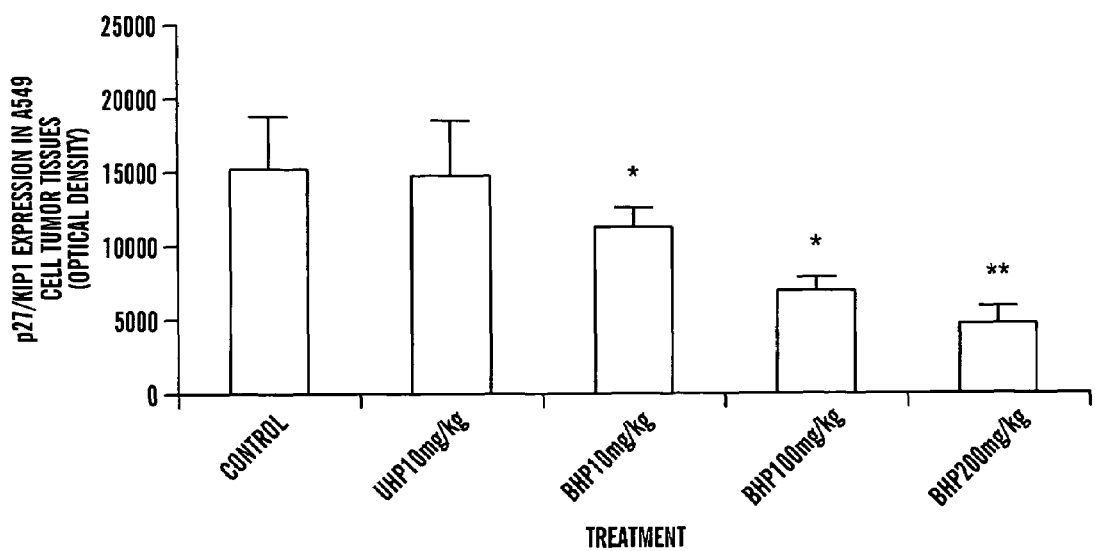
FIG. 20 shows expression of p27/KIP1 gene product in the A549 cell tumor tissue grown in SCID mice treated with heparins. BHP significantly inhibited p27/KIP1 in a dose dependent manner.
Figure 20:
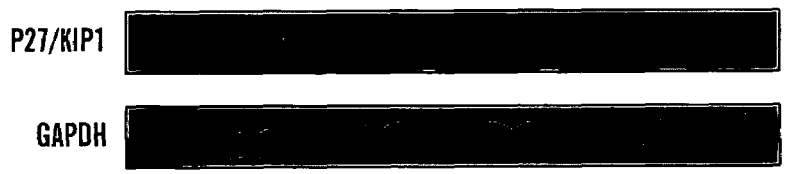
Figure 21:
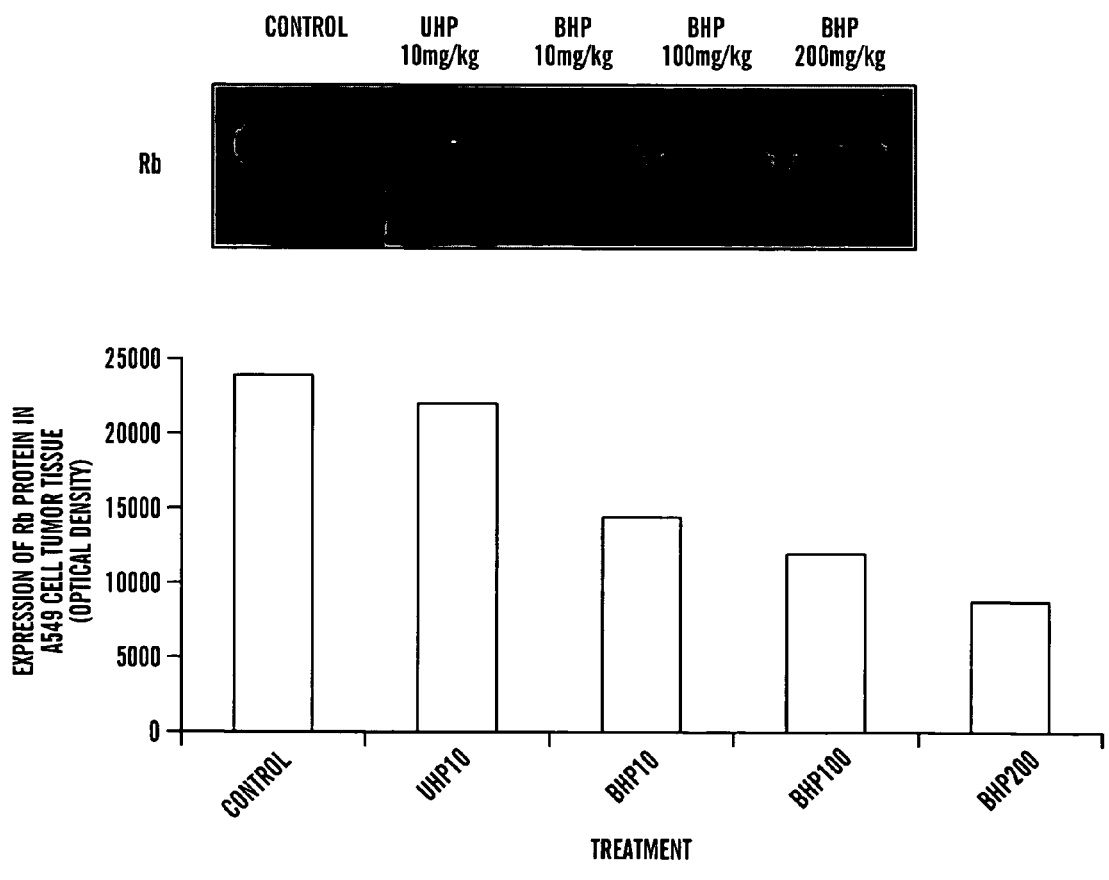
FIG. 21 shows expression of Rb gene product in the A549 cell tumor tissue grown in SCID mice treated with heparins. BHP decreased Rb gene expression in a dose dependent manner although to a lesser effect than on p27/KIP1.
Figure 22:
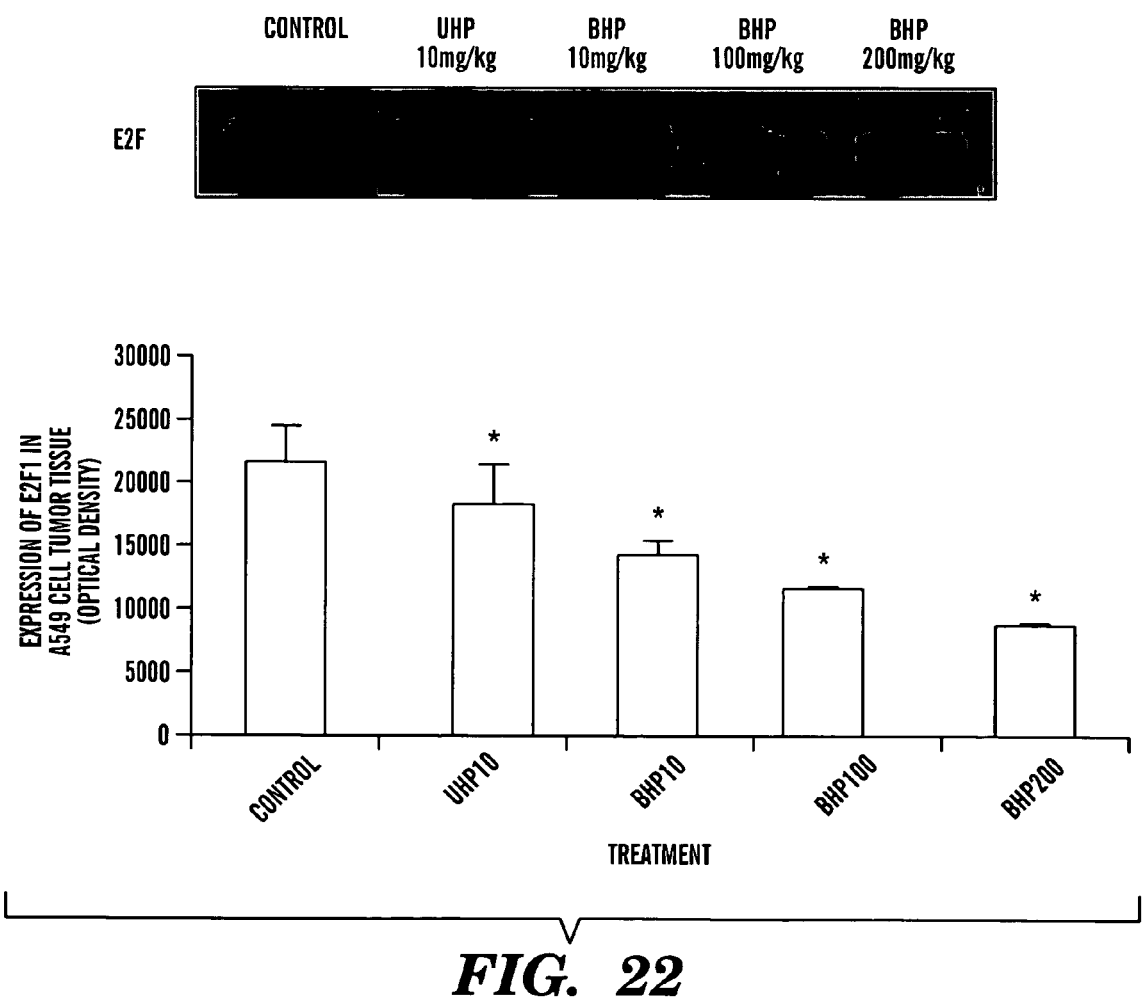
FIG. 22 shows expression of E2F1 protein in A549 cell tumor tissue grown in SCID mice treated with heparins. BHP significantly inhibited E2F1 protein expression in a dose dependent manner.

FIGS. 13 and 14 demonstrate that the above butanoylated heparin compounds exhibit very low anticoagulant effects (compared to non-acylated controls). Butanoylated heparin had no toxic effect on heart, liver, kidney, and lung of the animals tested (FIG. 15-18). Furthermore, the anti-tumor effect of butanoylated heparin is associated with the induction of apoptosis (FIG. 19). The mechanism by which butanoylated heparin inhibits tumor growth of lung cancer and colon-cancer may involve p27- and p21-RB-E2F pahthway (FIG. 20-22). Similar antiproliferative effects were seen with O-hexanoylated LMW heparin on anti-tumor cell growth in vitro.

TABLE 1

Assignment of selected signals in the $^1$H NMR spectrum of the O-hexanoyl heparin derivative.

| Residue | Chemical (ppm) shift | | | | |
|---|---|---|---|---|---|
| | H-1 | H-2 | H-3 | H-4 | H-5 |
| GlcNS6S | 5.302 | 3.093 | 3.539 | 3.629 | 3.892 |
| IdoA2S | 5.092 | 4.218 | 4.008 | 3.920 | 4.709 |

The invention claimed is:

1. A method of treating a malignancy or cancer of the colon comprising: providing an effective amount of an O-acylated heparin near or into a site of a tumor of the colon, to thereby decrease in size, or cease the growth of the malignancy or cancer of the colon.

2. The method of claim 1, wherein the O-acylated heparin is an O-hexanoylated heparin derivative.

3. The method of claim 1, wherein the O-acylated heparin is an O-butanoylated heparin derivative.

4. The method of claims 1, 2, or 3, wherein the malignancy or cancer of the colon is colon cancer.

* * * * *